US012364865B2

(12) United States Patent
DeShazo et al.

(10) Patent No.: US 12,364,865 B2
(45) Date of Patent: Jul. 22, 2025

(54) NEUROMODULATION THERAPY WITH A MULTIPLE STIMULATION ENGINE SYSTEM

(71) Applicant: Advanced Neuromodulation Systems, Inc., Plano, TX (US)

(72) Inventors: Daran DeShazo, Lewisville, TX (US); Steven Boor, Plano, TX (US); Gavin L Rade, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 838 days.

(21) Appl. No.: 16/790,443

(22) Filed: Feb. 13, 2020

(65) Prior Publication Data

US 2021/0252291 A1    Aug. 19, 2021

(51) Int. Cl.
*A61N 1/372* (2006.01)
*A61B 5/24* (2021.01)
(Continued)

(52) U.S. Cl.
CPC ............ *A61N 1/36185* (2013.01); *A61B 5/24* (2021.01); *A61B 18/14* (2013.01); *A61N 1/025* (2013.01);
(Continued)

(58) Field of Classification Search
CPC .. A61N 1/025; A61N 1/0551; A61N 1/36062; A61N 1/36125; A61N 1/36128; A61N 1/36142; A61N 1/378
See application file for complete search history.

(56) References Cited

U.S. PATENT DOCUMENTS 7,450,987 B2 *  11/2008  Varrichio ................ H02M 3/07
                                                          607/2
2006/0259098 A1    11/2006  Erickson
(Continued)

FOREIGN PATENT DOCUMENTS

CN    110327547 A    10/2019
CN    110433394 A    11/2019
WO    2018/136886 A1    7/2018

OTHER PUBLICATIONS

Patent Cooperation Treaty, International Search Report and Written Opinion Issue for PCT Application No. PCT/US2021/017914, dated Apr. 28, 2021, 7 pages.
(Continued)

*Primary Examiner* — Allen Porter
(74) *Attorney, Agent, or Firm* — Norton Rose Fulbright US LLP

(57) ABSTRACT

An implantable medical device (IMD) includes multiple stimulation engines (SEs) for independently stimulating respective electrode sets of a lead system. A voltage multiplier (VM) is configured to generate an adjustable target voltage at an output node. Each stimulation engine includes first switching circuitry to switchably connect an anodic node of the SE to the VM output node and second switching circuitry to switchably connect a cathodic node of the SE to a current sink circuit. Discharge switching circuitry may be disposed between the anodic and cathodic nodes of each SE. A selector and associated digital control logic block are operative to generate control signals for independently controlling respective SEs such that each SE may be activated to stimulate or discharge a corresponding select set of electrodes independently from or in concert with remaining SEs.

12 Claims, 16 Drawing Sheets

(51) Int. Cl.
   *A61B 18/14* (2006.01)
   *A61N 1/02* (2006.01)
   *A61N 1/05* (2006.01)
   *A61N 1/36* (2006.01)
   *A61N 1/362* (2006.01)
   *A61N 1/39* (2006.01)
   *A61N 2/00* (2006.01)
   *A61B 18/00* (2006.01)

(52) U.S. Cl.
   CPC ....... *A61N 1/0534* (2013.01); *A61N 1/36003* (2013.01); *A61N 1/36038* (2017.08); *A61N 1/36053* (2013.01); *A61N 1/36062* (2017.08); *A61N 1/36171* (2013.01); *A61N 1/36175* (2013.01); *A61N 1/362* (2013.01); *A61N 1/39622* (2017.08); *A61N 2/006* (2013.01); *A61B 2018/00577* (2013.01)

(56) References Cited

U.S. PATENT DOCUMENTS

| | | |
|---|---|---|
| 2008/0082137 A1 | 4/2008 | Kieval et al. |
| 2009/0048643 A1* | 2/2009 | Erickson ............... A61N 1/378 607/59 |
| 2009/0259278 A1 | 10/2009 | Torgerson et al. |
| 2010/0042187 A1 | 2/2010 | Werder et al. |
| 2010/0106231 A1 | 4/2010 | Torgerson et al. |
| 2010/0256712 A1 | 10/2010 | Varrichio et al. |
| 2011/0106213 A1 | 5/2011 | Davis et al. |
| 2011/0160799 A1 | 6/2011 | Mishra et al. |
| 2012/0271378 A1 | 10/2012 | Van Campen et al. |
| 2012/0286841 A1 | 11/2012 | Tranchina et al. |
| 2013/0261703 A1 | 10/2013 | Chow et al. |
| 2013/0282079 A1* | 10/2013 | Kallmyer ........... A61N 1/36125 607/62 |
| 2013/0318259 A1 | 11/2013 | Sherman |
| 2014/0350623 A1 | 11/2014 | Fischer et al. |
| 2015/0224317 A1 | 8/2015 | Torgerson |
| 2016/0158549 A1 | 6/2016 | Woods et al. |
| 2018/0214048 A1 | 8/2018 | Zdeblick et al. |
| 2019/0381316 A1 | 12/2019 | Rozgic et al. |
| 2020/0147389 A1 | 5/2020 | Boor et al. |
| 2020/0306533 A1 | 10/2020 | DeShazo et al. |
| 2020/0306543 A1 | 10/2020 | Boor et al. |
| 2020/0346005 A1 | 11/2020 | Boor et al. |

OTHER PUBLICATIONS

Patent Cooperation Treaty, International Search Report and Written Opinion issued for PCT Application No. PCT/US2021/015949, dated Apr. 21, 2021, 14 pages.

European Patent Office, Communication, Extended European Search Report issued for European Patent Application No. 21746910.5, dated Dec. 11, 2023, 6 pages.

European Patent Office, Communication, Extended European Search Report issued for European Patent Application No. 21753045.0, dated Dec. 19, 2023, 6 pages.

* cited by examiner

GENERATING, FOR EACH RESPECTIVE STIMULATION ENGINE, A FIRST CONTROL SIGNAL FOR CONTROLLING THE FIRST SWITCHING CIRCUITRY, A SECOND CONTROL SIGNAL FOR CONTROLLING THE SECOND SWITCHING CIRCUITRY AND A THIRD CONTROL SIGNAL FOR CONTROLLING THE DISCHARGE CIRCUITRY OF THE RESPECTIVE STIMULATION ENGINE

PROVIDING, FOR EACH STIMULATION ENGINE, A CURRENT SOURCE CIRCUIT, WHEREIN THE FIRST SWITCHING CIRCUITRY IS ARRANGED TO SWITCHABLY CONNECT THE ANODIC NODE OF THE STIMULATION ENGINE TO THE VM OUTPUT NODE VIA THE CURRENT SOURCE CIRCUIT

— 1032

GENERATING, FOR EACH RESPECTIVE STIMULATION ENGINE, A FIRST PAIR OF CONTROL SIGNALS FOR CONTROLLING THE FIRST SWITCHING CIRCUITRY, A SECOND PAIR OF CONTROL SIGNALS FOR CONTROLLING THE SECOND SWITCHING CIRCUITRY, THE SECOND PAIR OF CONTROL SIGNALS HAVING COMPLEMENTARY LOGIC LEVELS WITH RESPECT TO THE FIRST PAIR OF CONTROL SIGNALS, AND A THIRD CONTROL SIGNAL FOR CONTROLLING THE DISCHARGE CIRCUITRY OF THE RESPECTIVE STIMULATION ENGINE

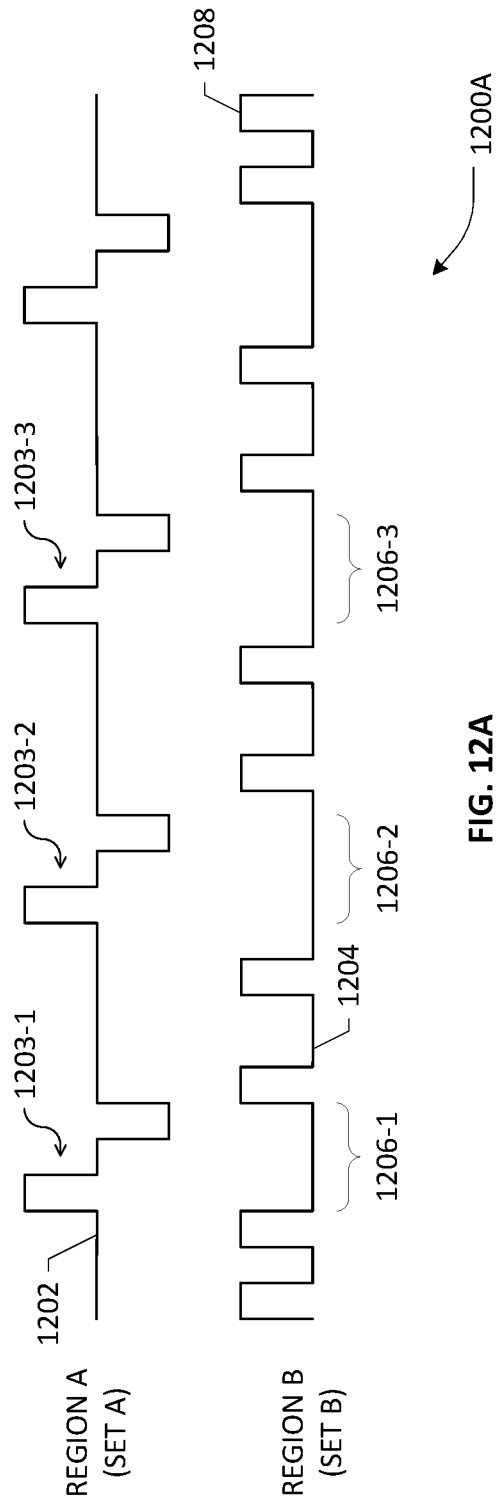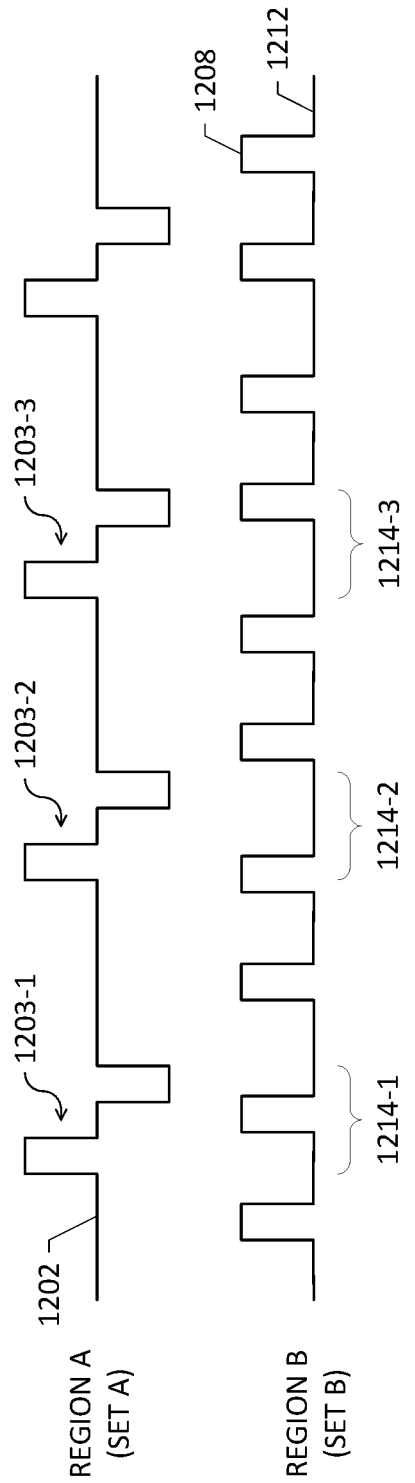

NEUROMODULATION THERAPY WITH A MULTIPLE STIMULATION ENGINE SYSTEM

CROSS-REFERENCE TO RELATED APPLICATION(S)

This application discloses subject matter that is related to the subject matter of the following U.S. patent application(s): (i) "IMPLANTABLE PULSE GENERATOR WITH MULTIPLE STIMULATION ENGINES", application Ser. No. 16/778,255, filed Jan. 31, 2020 in the name(s) of Steven Boor et al.; each of which is hereby incorporated by reference in its entirety.

TECHNICAL FIELD

The present disclosure generally relates to implantable pulse generators and stimulation circuitry used in association with neurostimulation systems (NS) including but not limited to spinal cord stimulation (SCS) systems.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more multi-electrode leads. A typical RF system configuration comprises a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Whereas advances in IPG systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to IPG systems having multiple stimulation engines and selectively connectable power supply circuitry associated therewith for independently stimulating respective electrode sets of a lead system having one or more implantable leads. In one arrangement, a voltage multiplier (VM) is configured to generate an adjustable target voltage at an output node. A plurality of stimulation engines are provided, wherein each stimulation engine (SE) includes first switching circuitry to switchably connect an anodic node of the SE to the VM output node and second switching circuitry to switchably connect a cathodic node of the SE to a current sink circuit. Discharge switching circuitry may be disposed between the anodic and cathodic nodes of each SE. A selector and associated digital control logic block are operative to generate control signals for independently controlling respective SEs so that each SE may be activated to stimulate or discharge a corresponding select set of electrodes independently from or in concert with the remaining SEs.

In one aspect, an embodiment of the present patent disclosure is directed to an implantable medical device (IMD), which comprises, inter alia, a power supply; a lead system comprising one or more leads configured to be positioned proximate to a patient's tissue, wherein each lead includes a plurality of electrodes; and a voltage multiplier (VM) configured to generate an adjustable target voltage at an output node based on a voltage supplied by the power supply, which may be commonly and switchably coupled to a plurality of stimulation engines. In one arrangement, each respective SE includes an anodic node; first switching circuitry configured to switchably connect the anodic node to the VM output node; a cathodic node; a current sink circuit switchably coupled to the cathodic node; second switching circuitry configured to actuate switchable coupling between the current sink circuit and the cathodic node; and discharge switching circuitry coupled or otherwise disposed between the cathodic and anodic nodes. The IMD may comprise a multiplexer/selector logic block configured to selectively couple the anodic node and the cathodic node of a respective stimulation engine to a select set of the electrodes for applying a stimulation therapy to the patient's tissue according to a stimulation set. The IMD may comprise a digital control logic block configured to generate a plurality of control signals for independently controlling respective stimulation engines such that each stimulation engine is activated to stimulate or discharge a corresponding set of electrodes independently from the remaining stimulation engines. In one arrangement, the digital control logic block of the IMD may comprise circuitry to generate, for each respective stimulation engine, a first control signal for controlling the first switching circuitry, a second control signal for controlling the second switching circuitry and a third control signal for controlling the discharge switching circuitry of the respective stimulation engine, wherein the first, second and third control signals have appropriate logic levels for assertion/de-assertion with respect to performing stimulation and discharge operations.

In another embodiment, an example IMD may be arranged such that each stimulation engine may also include a current source circuit on the anodic side in addition to the foregoing components in order to provide additional stimulation selection and discharge flexibility. In this embodiment, the first switching circuitry may be arranged to switchably connect the anodic node of the stimulation engine to the VM output node via the current source circuit. Further, the digital control logic block of an IMD according to such embodiment comprises circuitry to generate, for each respective stimulation engine, a first pair of control signals for controlling the first switching circuitry, a second pair of control signals for controlling the second switching circuitry, the second pair of control signals having complementary logic levels with respect to the first pair of control signals, and a third control signal for controlling the discharge switching circuitry of the respective stimulation engine, wherein appropriate logic levels may be asserted or de-asserted for the control signals with respect to performing stimulation and discharge operations on a per engine basis.

In another aspect, an embodiment of the present patent disclosure is directed to a stimulation therapy method using an IMD including a power supply and a lead system of one or more leads configured to be positioned proximate to a patient's tissue, wherein each lead includes a plurality of electrodes. The example method comprises, inter alia, providing a voltage multiplier (VM) configured to generate a range of target voltages at an output node based on a voltage supplied by the power supply; and providing a plurality of stimulation engines (SEs), each being switchably/selectably connectable to the VM output node. Each SE is configured to support an anodic node and a cathodic node, wherein the anodic node is switchably connectable by first switching circuitry to the VM output node, either via or without a current source circuit, and the cathodic node is switchably connectable by second switching circuitry to a current sink circuit operative to drive the cathodic node, each SE further including discharge switching circuitry coupled or otherwise disposed between the anodic node and the cathodic node thereof. The method further includes selectively coupling one or more sets of electrodes of the lead system to a corresponding number of SEs at respective anodic and cathodic nodes under suitable selector control logic depending on a therapy application; and generating a plurality of control signals for independently controlling respective stimulation engines such that each selected stimulation engine is activated to stimulate or discharge a corresponding set of electrodes independently from the remaining stimulation engines for applying a stimulation therapy to the patient tissue according to a stimulation set, wherein unintended current flow due to at least one of channel contention or electrical collision between the respective sets of electrodes of the lead system is avoided. Channel contention or electrical collisions can occur when multiple stimulation engines require simultaneous usage of one or more of the same electrodes, or when the multiple SEs would normally require different voltage multiplier settings at the same time.

Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 10A-10C depict flowcharts of blocks, steps and/or acts that may be (re)combined in one or more arrangements for facilitating a stimulation therapy method with multiple stimulation engines of a biostimulation system according to some embodiments of the present disclosure;

FIGS. 12A and 12B each depict a panel of illustrative waveforms associated respectively with a single engine stimulation therapy based on pulse shifting and a two-engine stimulation therapy according to an embodiment of the present patent disclosure.

DETAILED DESCRIPTION

Figure 1A:
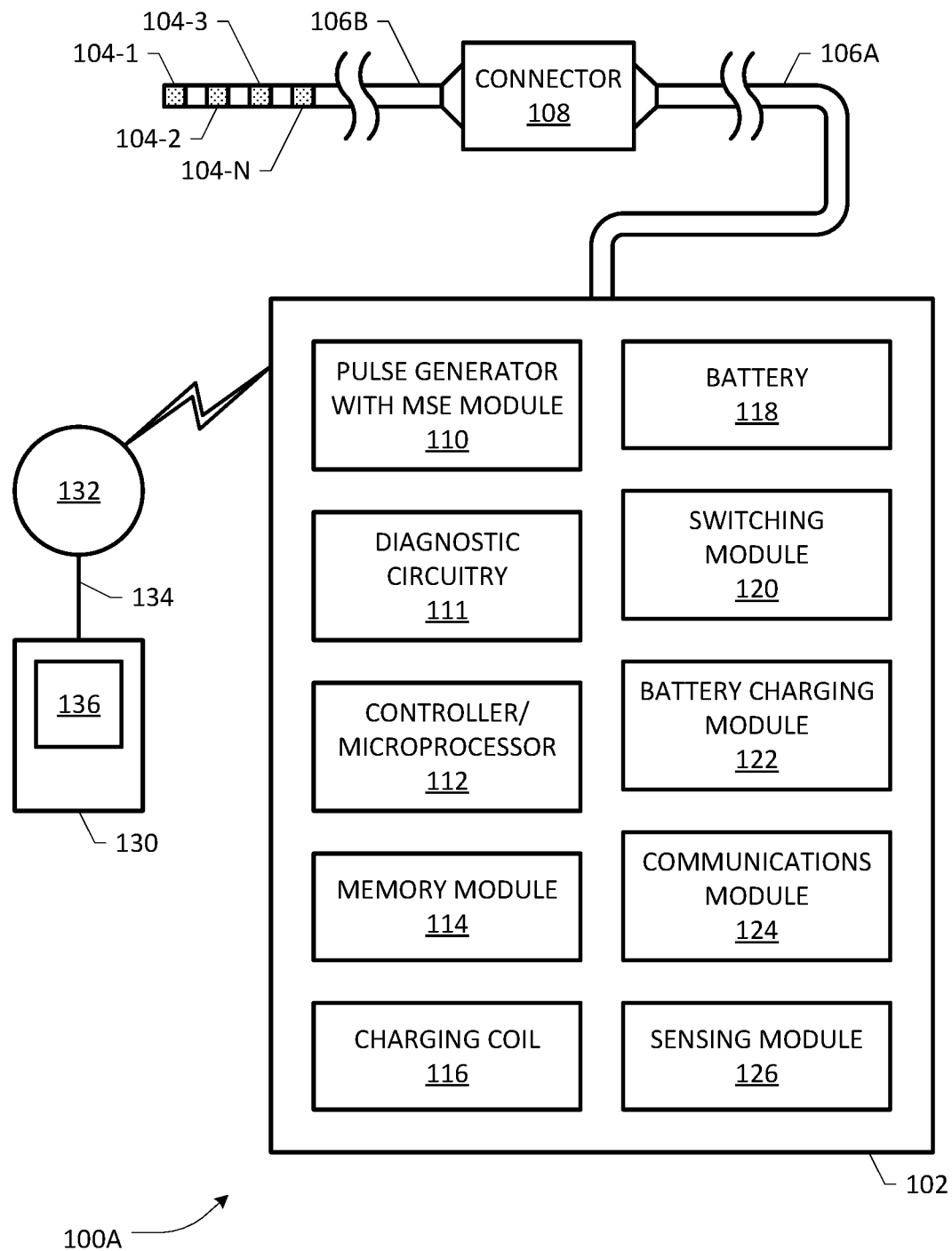
FIG. 1A depicts an example biostimulation system wherein an embodiment of an implantable medical device (IMD) with multiple stimulation engines (MSEs) of the present disclosure may be practiced according to the teachings herein.

In the description herein for embodiments of the present disclosure, numerous specific details are provided, such as examples of circuits, devices, components, and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) for generating electrical stimulation according to one or more multiple stimulation sets for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system 100A wherein an embodiment of an implantable medical device (IMD) with multiple stimulation engines of the present disclosure may be practiced according to the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A comprises an implantable pulse generator (IPG) or IMD 102 having a pulse generator portion including multiple stimulations engines adapted to provide independent therapies simultaneously without channel collision as will be set forth in additional detail further below. In one example embodiment, IMD 102 may be implemented as having a metallic housing or can that encloses a controller/processing block or module 112, pulse generating circuitry with multiple stimulation engine (MSE) module 110, a charging coil 116, a battery/power supply 118, a far-field and/or near field communication block or module 124, battery/power supply charging circuitry 122, switching circuitry 120, sensing circuitry 126, a memory module 114, and the like. Controller/processor module 112 typically includes a microcontroller or other suitable processor for controlling the various other components of IMD 102. Software/firmware code may be stored in memory 114, which may be integrated with the controller/processor module 112, and/or other suitable application-specific storage components (not particularly shown in this FIG.) for execution by the microcontroller or processor 112 and/or other programmable logic blocks to control the various components of IMD 102 for purposes of an embodiment of the present patent disclosure.

In one arrangement, IMD 102 may be coupled to a separate or an attached extension component 106A for providing electrical and physical connectivity to a lead system via a lead connector 108, wherein one or more leads each having a respective plurality of electrodes may be provided. By way of example, a single lead 106B is illustrated, wherein a distal end of the single lead 106B includes a plurality of electrodes 104-1 to 104-N. Where the extension component 106A is provided as a separate component, the extension component 106A may connect with a "header" portion of IPG/IMD 102 as is known in the art. If the extension component 106A is integrated with IMD 102, internal electrical connections may be made through respective conductive components. In general operation, electrical pulses are generated by the pulse generating circuitry 110 under the control of processing block 112, and are provided to the switching circuitry 120 that is operative to selectively connect to electrical outputs of the IMD, which are ultimately coupled to the electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may comprise one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERING THE SAME", which is incorporated herein by reference.

In one arrangement, the lead system 106B (including extension 106A where provided) may comprise a lead body of insulative material encapsulating a plurality of conductors within the material that extend from a proximal end (that is proximate to IMD 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IMD 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur in some embodiments through the lead electrodes 104-1 to 104-N, corresponding conductors, and associated terminals. By way of illustration, an example embodiment of the stimulation system 100A may be provided with one or more leads, each having a plurality of lead electrodes 104-1 to 104-N comprising four electrodes, eight electrodes, etc., although any suitable number of electrodes (as well as corresponding conductive traces and terminals), wherein the leads may be configured to be positioned proximate to a patient's tissue at one or more locations for providing independent stimulation therapies according to the teachings herein. Additionally, alternatively, or optionally, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IMD 102, such as, e.g., processor and associated charge control circuitry for pulse generation, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IMD using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided for operation in association with respective current regulation circuitry as part of individual stimulation engines of module 110 for independently energizing different portions or sets of the electrodes of the lead system. In some example embodiments, different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that may include selective stimulation therapy treatments through one or more leads or electrodes 104-1 to 104-N as is also known in the art. Various sets of parameters may define the pulse characteristics and pulse timing for the pulses applied to the various lead electrodes as is known in the art. It should be appreciated that although constant current pulse generating circuitry is contemplated for some embodiments, any other suitable type of pulse generating circuitry may be employed in association with a multi-stimulation engine arrangement of the present invention.

In an example implementation of IMD 102, sensing circuitry 126 may be optionally provided, preferably adapted to measure a suitable electric parameter or transduced characteristic (e.g., voltage, current, capacitance, etc.) over a configurable or select time associated with the stimulation target or tissue through at least one of the electrodes proximate to the stimulation target. For example, the sensing circuitry 126 may measure an evoked compound activation potential (ECAP) waveform from an Aβ sensory fiber or spinal cord. Optionally, the sensing circuitry 126 may store the measured/sensed electric data in memory 114. Furthermore, diagnostic circuitry 111 may be configured to interoperate with the sensing circuitry 126 and pulse generation and switching functionalities of IMD 102 for generating suitable diagnostic control signals that may be configured to adjustably control the operation of an MSE arrangement for purposes of the present invention as will set forth further below in additional detail.

An external device 130 may be implemented to charge/recharge the battery/power supply 118 of IMD 102 (although a separate recharging device could alternatively be employed), to access memory 114, and/or to program or reprogram IMD 102 with respect to the stimulation set parameters including pulsing specifications while implanted within the patient. In alternative embodiments, however, separate programmer devices may be employed for charging and/or programming IMD 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IMD 102. Optionally, in some embodiments, the wand 134 may comprise one or more temperature sensors for use during charging operations.

In general operation, a user (e.g., a doctor, a medical technician, or the patient) may initiate communication with IMD 102 by placing the wand 134 proximate to the stimulation system 100A. Preferably, the placement of the wand 134 allows the telemetry system to be aligned with the far-field and/or near field communication circuitry 124 of IMD 102. The external device 130 preferably provides one or more user interfaces 136 (e.g., touch screen, keyboard, mouse, buttons, scroll wheels or rollers, or the like), allowing the user to operate IMD 102. The external device 130 may be controlled by the user through the user interface 136, allowing the user to interact with IMD 102, including, e.g., effectuating programmatic control for dynamically configuring stimulation current pulses as well as independent selection/activation of different stimulation engines in some embodiments. Further, the user interface 136 may permit the user to move electrical stimulation along and/or across one or more of the lead(s) 106A/B using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which sets or subsets of electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally, some electrodes of the lead system 106/A/B may be configured to operate as current sink terminals or cathodes whereas other electrodes may be configured as current source terminals or anodes. Additionally or alternatively, the external device 130 may access or download the electrical measurements from the memory 114 acquired by the sensing circuitry 126.

In some embodiments, the external programmer device 130 may permit operation of IMD 102 according to one or more stimulation therapy programs or applications (e.g., an SCS application) to treat the patient. Each therapy program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulsing, monophasic pulsing, etc. IMD 102 may be configured to modify its internal parameters in response to the control signals from the external device 130 to vary the stimulation pulse characteristics of the respective stimulation therapies delivered by the multiple stimulation engines and transmitted through the selected portions of the electrodes of lead system 106A/106B to the tissue of the patient. Example stimsets and multi-stimset programs that may be used in association with one or more stimulation engines of the present invention may be found in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

Figure 1B:
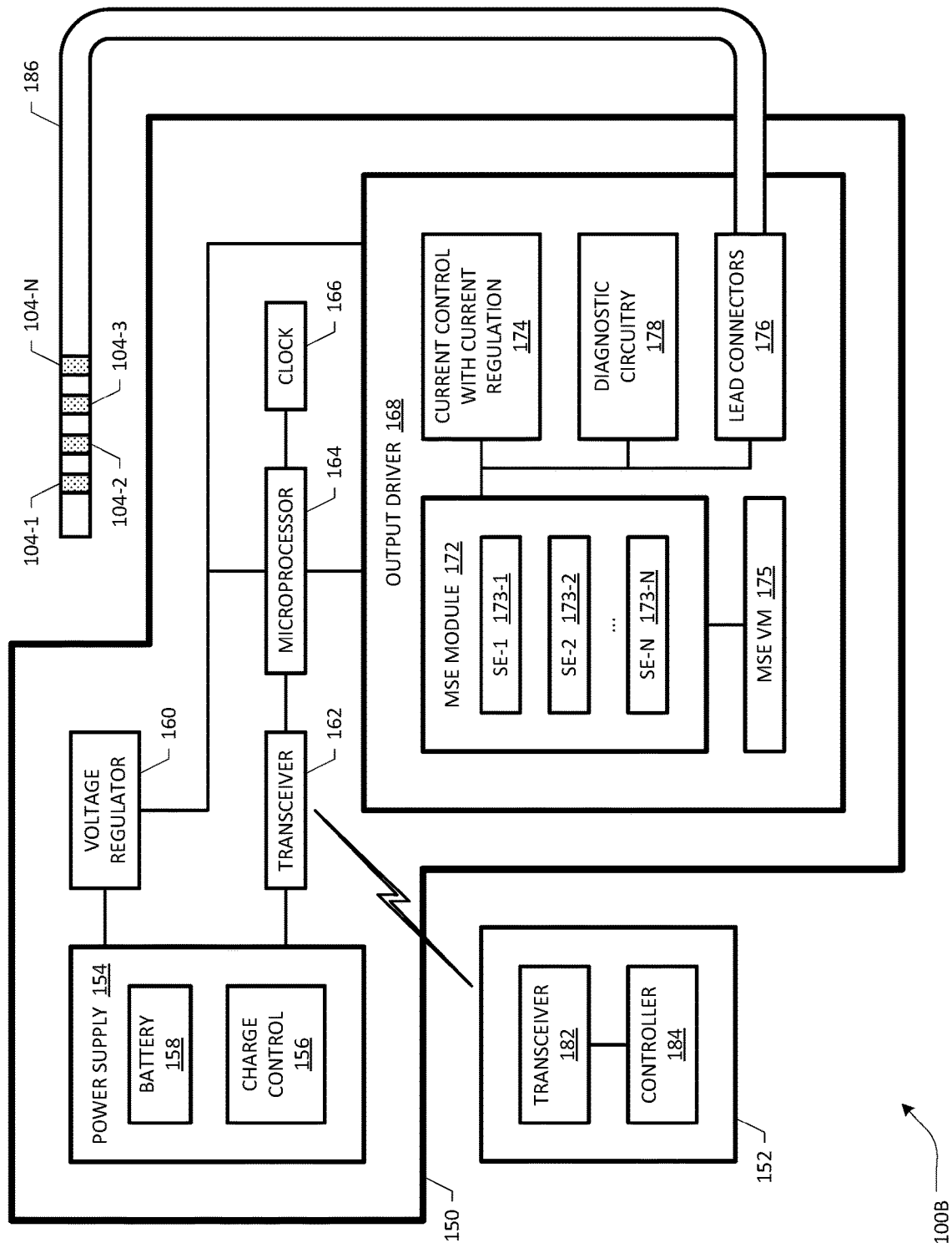
FIG. 1B depicts another view of a biostimulation system that illustrates additional details of an IMD's pulse generator including a plurality of stimulation engines for providing multiple stimulation therapies according to an embodiment of the present disclosure.

FIG. 1B depicts another embodiment of a biostimulation system 100B that illustrates additional details of an example IMD's pulse generator including a plurality of stimulation engines for simultaneously and/or selectively providing multiple stimulation therapies without channel collision or contention according to an embodiment of the present disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to the external device 130 described in the foregoing sections. IPG 150 may be implanted within the body of a human or animal patient (not shown) for providing electrical stimulation from IPG 150 to a selected area of the body via lead 186 under control of external programmer/controller 152. It should be appreciated that although lead 186 is illustrated to provide a stimulation portion of stimulation system 100B configured to provide stimulation remotely with respect to the generator portion 150 of stimulation system 100B, a lead as described herein is intended to encompass a variety of stimulation portion configurations including, e.g., a microstimulator electrode disposed adjacent to a generator portion.

Furthermore, although example lead systems 186 and 106A/B shown in FIGS. 1A/1B are exemplified as a single implantable lead, the teachings herein are not necessarily limited thereto. An example embodiment of the present invention may involve a lead system comprising two or more implantable leads, with each lead having a respective plurality of electrodes, wherein different combinations of electrodes/leads may be grouped into one or more channels in a stimulation therapy system. Stimulation current pulses according to different therapies may be applied by respective stimulation engines to different portions of electrodes according to a particular channel selection scheme regardless of whether one or more leads and/or one or more sets of electrodes are selected for stimulation.

IPG 150 may be configured as a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, microcontroller (or microprocessor) 164, clock 166, and output driver circuitry 168 comprising MSE module 172 having a plurality of stimulation engines (SEs) 173-1 to 173-N, each having respective current regulation circuitry, switchable connectivity to a voltage multiplier (e.g., VM 175) as well as discharge switching circuitry, which will be described in further detail below. Alternatively or additionally, a separate current control/regulation block 174 along with a switchable voltage multiplier may be provided in some embodiments for operation with MSE module 172. Further, suitable diagnostic circuitry 178 may also be provided as part of output driver 168 in some embodiments.

Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide recharging management with respect to battery 158. Transceiver 162 of an example embodiment of IPG 150 is operative to provide data/control communication between microprocessor 164 and a controller 184 of external programmer/controller 152, via transceiver 182 provided therewith. Transceiver 162 of an example embodiment, in addition to or in the alternative to providing data/control communication, may provide a conduit for delivering energy to power supply 158 via RF or inductive recharging as previously noted.

Microprocessor/controller 164 provides overall control with respect to the operation of IPG 150, such as in accordance with a program stored therein or provided thereto by external programmer/controller 152. One or more SEs 173-1 to 173-N of MSE module 172 may be configured to generate and deliver stimulation therapies having suitable pulse characteristics to selected sets or portions of electrodes 104-1 to 104-N under control of microcontroller 164. In general operation, for example, different SEs 173-1 to 173-N of MSE module 172 may be controlled to output optimized stimulation therapies simultaneously without collisions to different sets of electrodes selected under programmatic control. By way of illustration, a stimulation therapy may comprise delivering a constant current pulse of a desired magnitude/amplitude, duration, phase, and frequency to a tissue load present with respect to particular ones/sets of electrodes 104-1 to 104-N, which may be represented as respective lumped-element electrode/tissue interface (ETI) loads. Clock 166 preferably provides system timing information, such as may be used by microcontroller 164 in controlling system operation, as well as for different portions of MSE module 172 and/or VM 175 in generating desired voltages, controlling switchable connectivity to VM 175, etc., described below in further detail.

Lead system 186 of the illustrated embodiment includes a lead body encapsulating a plurality of internal conductors coupled to lead connectors (not shown) to interface with lead connectors 176 of IPG 150 in a hermetically sealed arrangement. The internal conductors provide electrical connection from individual lead connectors to each of a corresponding one of electrodes 104-1 to 104-N, which may be configured to provide anodic current stimulation and/or cathodic current stimulation for application at, or proximate to, a spinal nerve or peripheral nerve, brain tissue, muscle, or other tissue depending on a desired therapy. As will be seen below, individual SEs 173-1 to 173-N may be configured to provide separate stimulation currents while delivering respective therapies simultaneously. Stated differently, example SEs 173-1 to 173-N may be independently controlled to output respective electrical signals by varying signal parameters such as intensity, duration and/or frequency in order to deliver a desired therapy and/or otherwise provide optimal stimulation current pulsing as described herein.

Skilled artisans will recognize that any number of electrodes, and corresponding conductors, may be utilized according to some embodiments, as previously noted. Moreover, various types, configurations and shapes of electrodes (and lead connectors) may be used according to some embodiments. An optional lumen (not shown) may extend through the lead 186, such as for use in delivery of chemicals or drugs or to accept a stylet during placement of the lead within the body of a patient. Additionally or alternatively, the lead system (stimulation portion) and IPG (generator portion) may comprise a unitary construction, such as that of a microstimulator configuration.

As mentioned above, programmer/controller 152 of an example embodiment provides data communication with IPG 150, such as to provide programmatic control, e.g., adjust stimulation settings, selection of SEs, selection and/or electrical polarity configuration of different groups of electrodes to which stimulation pulses are delivered, etc. An embodiment of a pulse generation system and the delivery of stimulation pulses that may be configured, *Mutatis mutandis*, to interoperate with multiple SEs of the present patent disclosure may be found in U.S. Pat. No. 6,609,031, entitled "MULTIPROGRAMMABLE TISSUE STIMULATOR AND METHOD", which is incorporated herein by reference.

In one example embodiment of IPG 150, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to provide a regulated supply $V_{OUT}$ within a range acceptable to circuitry of IPG 150, including output driver circuitry 168 having MSE module 172, associated voltage multiplier 175 and/or current control and current regulation 174 for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too close to or below the $V_{OUT}$, causing the voltage regulator output voltage to also fall. In such a situation, therefore, the regulator can no longer provide the desired regulated output voltage. However, voltage regulator 160 of an embodiment may be adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control in association with suitable control signaling. For example, sensing circuitry, such as may utilize an analog-to-digital converter (ADC) in making voltage measurements may be utilized according to a preferred embodiment to provide information with respect to the battery voltage, which may be used by a digital control system (e.g., supported by microcontroller 164) in order to provide appropriate control signals e.g., select signals, for controlling the output voltage of voltage regulator 160. Additional details regarding voltage regulation may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), which is hereby incorporated herein by reference.

Skilled artisans will recognize that although an embodiment of voltage regulation is set forth hereinabove, a variety of techniques and circuits may be provided for operation with an IPG having multiple SEs described below in a particular implementation. In general, any suitable voltage regulator/multiplier arrangement may be adapted to provide a dynamic voltage adjustment to cover the voltage levels required for different stimulation currents under different loads according to some example embodiments of the present disclosure.

Figure 2:
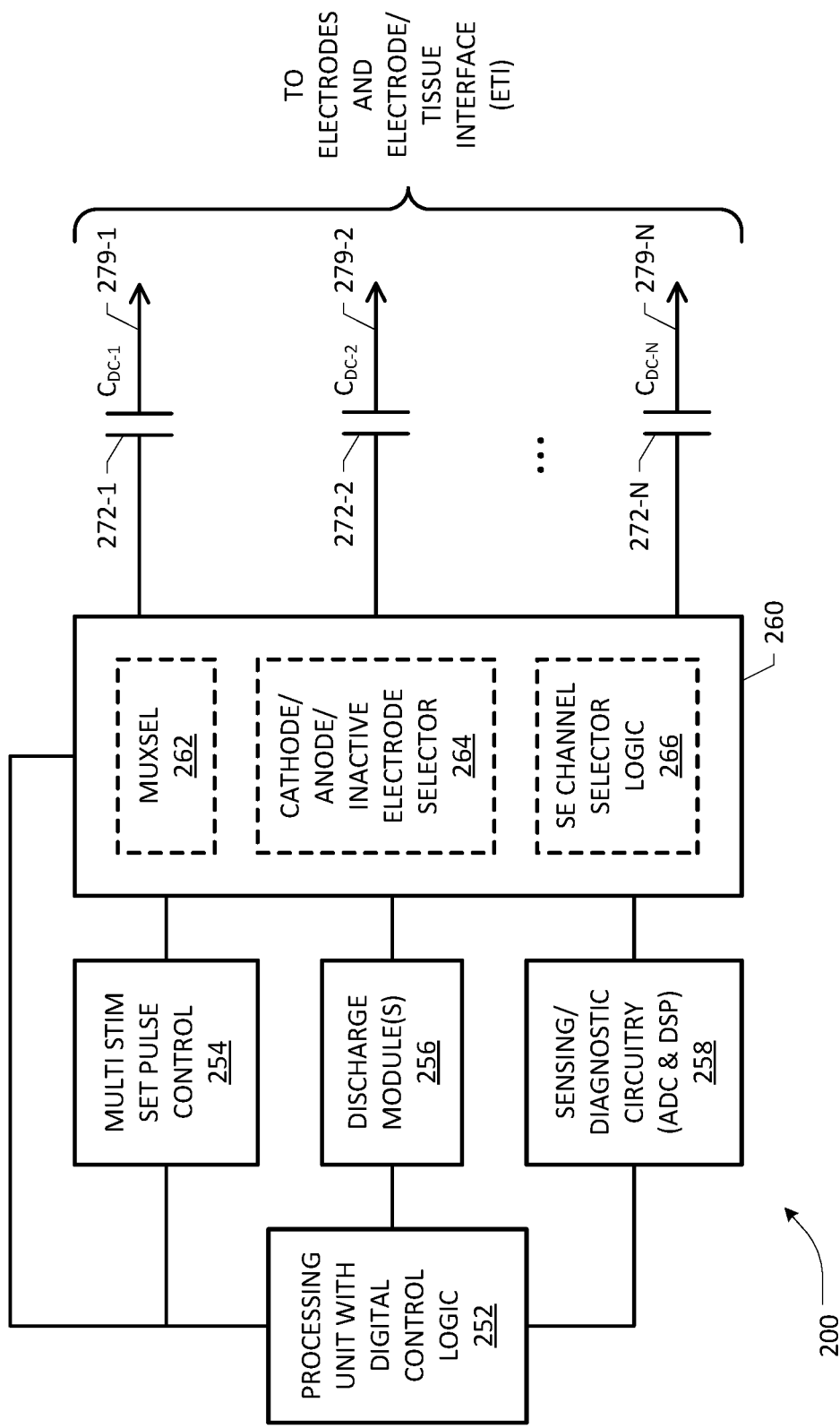
FIG. 2 depicts a block diagram of a pulse generator portion having multiple stimulation engine selection control and associated lead electrode arrangement according to an embodiment of the present disclosure.

FIG. 2 depicts a block diagram of a pulse generator portion 200 having multi-stimset pulse control, electrode and/or SE selection and configuration functionality and diagnostic circuitry, and associated lead electrode arrangement according to an embodiment of the present disclosure. One skilled in the art will recognize upon reference hereto that various functionalities associated with example blocks shown as part of the pulse generator portion 200 may be distributed and/or integrated among one or more blocks, subsystems and/or modules described hereinabove with respect to FIGS. 1A/1B. Consistent with the description provided previously, a processing unit 252 having or associated with suitable digital control logic is operatively coupled to multi SE pulse control module 254, one or more discharge modules 256 and sensing/diagnostic circuitry 258 for facilitating various functionalities including but not limited to voltage measurements, active discharge cycling, electrode selection and configuration, SE selection, etc. under appropriate programmatic/diagnostics control. An input/output (I/O) interface block 260 is operatively coupled to a plurality of lead connectors 279-1 to 279-N interfaced with respective electrodes, which interfaces may be modeled as suitable lumped-element ETI circuit representations, wherein the lead connectors and associated electrodes may be configured as one or more leads, each having a respective plurality of electrodes. Regardless of the number of leads, a lead connector 279-1 to 279-N may be provided with a DC blocking stimulation capacitor ($C_{DC}$) for facilitating direct current flow blocking functionality with respect to the corresponding electrode that may be configured to operate as a stimulation node. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC-1}$ 272-1 is coupled to lead connector 279-1. Likewise, remaining lead connectors 279-N may be provided with respective $C_{DC-N}$ 272-N to facilitate DC blocking with respect to each corresponding lead electrode thereof.

Interface block 260 may include appropriate multiplexing and selection circuitry 262 and anode/cathode/inactive electrode selection circuitry 264 for measurement and sensing/diagnostics purposes wherein different electrodes of an electrode grouping of the lead system may be selectively configured for stimulation (e.g., anodic or cathodic stimulation), sensing, or designating unused/inactive states, etc., with appropriate electrical connections being made within an IPG device accordingly relative to the various components therein. In some embodiments, portions of diagnostic circuitry 258 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Additional details regarding configuring lead electrodes as cathodes or anodes, either during stimulation or for discharging, may be found in may be found in the '643 patent application publication incorporated by reference hereinabove. Still further, an SE selection block 266 may be provided for selectively coupling a (sub)set or portion of lead connectors to a select one of the plurality of SEs under programmatic control, which selection may be mediated via an external programmer (e.g., a clinician programmer or a patient controller) as previously noted.

Figure 3:
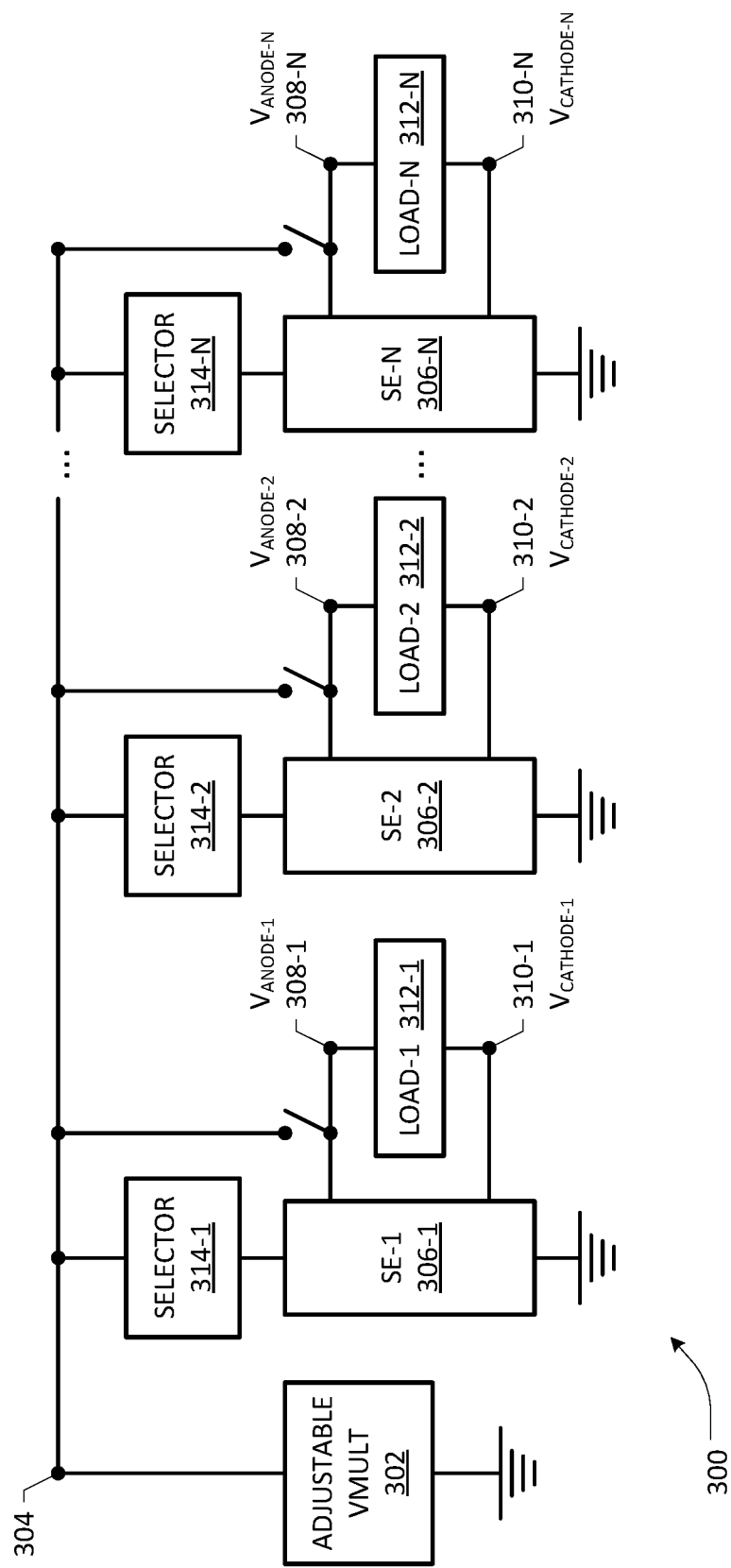
FIG. 3 depicts an example circuit arrangement having multiple stimulation engines that are switchably connectable to a voltage multiplier depending on electrode selection control according to an embodiment of the present disclosure.

FIG. 3 depicts an example circuit arrangement 300 having multiple stimulation engines that may be switchably connectable to a common voltage multiplier for driving different electrode sets depending on electrode selection control according to an embodiment of the present disclosure. An adjustable voltage multiplier (VMULT) 302 may be configured as a charge pump arrangement that can step up or step down from a regulated voltage supply, e.g., from a battery, to provide an output voltage that can cover up to a certain maximum voltage level ($V_{MAX}$) in order to support a sufficient voltage headroom (e.g., 12.0V to 20.0V) for different stimulation settings applicable for a therapy application. For example, a DRG application may require a lower $V_{MAX}$ level than an SCS or DBS application. In one arrangement, VMULT 302 may be implemented as a stacked charge pump capacitor arrangement to provide different output voltages at an output node 304. In general, VMULT 302 may be configured to operate as a voltage supply that may be commonly used by different SEs 306-1 to 306-N to apply stimulation to respective sets of electrodes of a lead system. As illustrated, a plurality of loads 312-1 to 312-N, each representing a respective set of electrodes, are coupled between an anodic node ($V_{ANODE}$) and a cathodic node ($V_{CATHODE}$) of a respective SE. In some embodiments, each SE may be provided with a selector logic module for selectively coupling and/or energizing a select set or portion of the electrodes as the respective load therefor. As shown in FIG. 3, selector logic modules 314-1 to 314-N are operative with respect to corresponding SE modules 306-1 to 306-N. In some embodiments, the overall selection logic functionality may be centrally or commonly provided with respect to all SE modules 306-1 to 306-N as part of an IMD's I/O interface block. Regardless of how the SE selection and/or electrode set selection is configured in an example embodiment, suitable digital control logic may be implemented to generate appropriate control signals for controlling/managing switchable connectivity with respect to each SE in order to couple the anodic node of a selected SE to the output node 304 of VMULT 302 for energizing a corresponding set of electrodes, as will be set forth in detail below.

Figure 4:
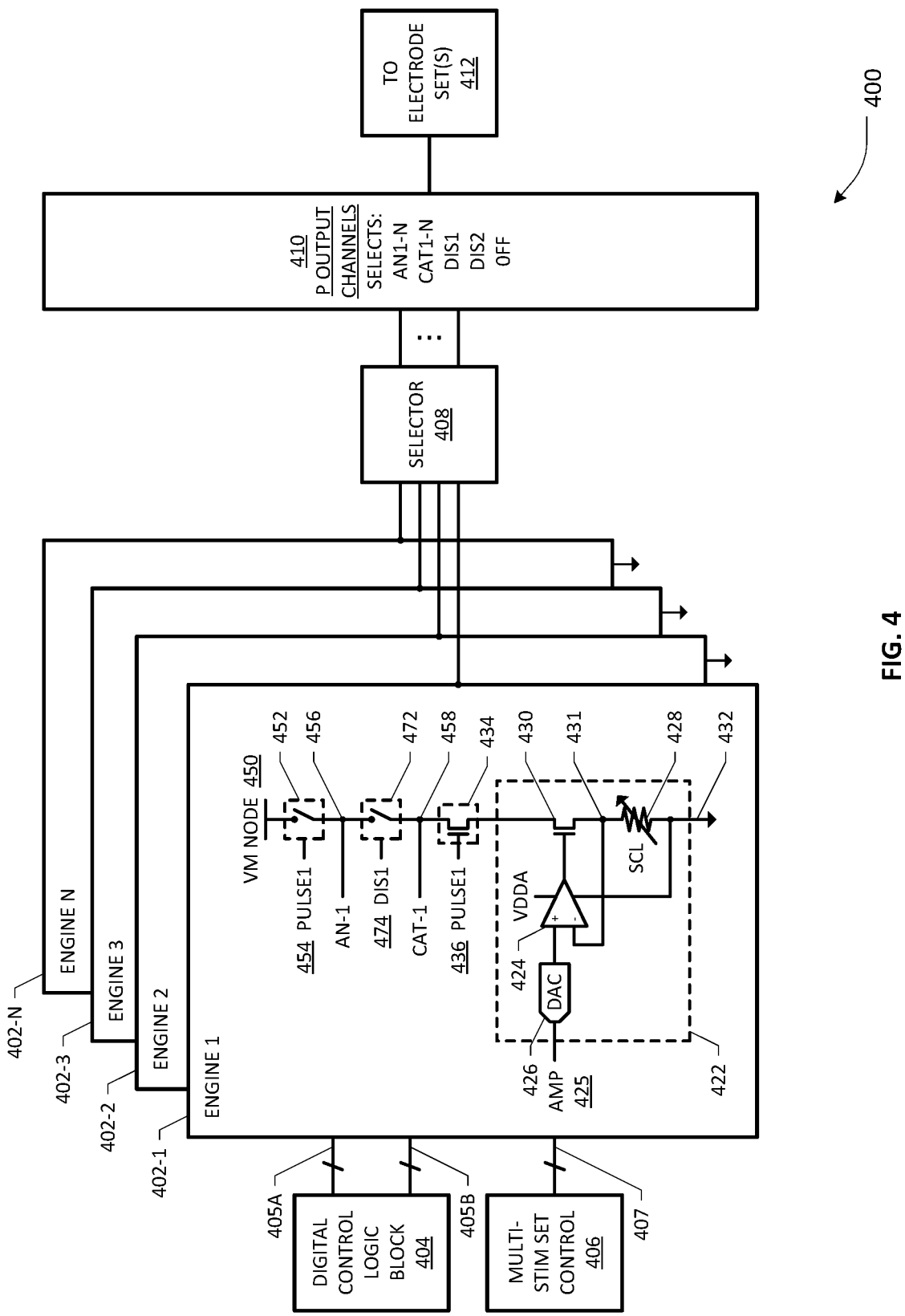
FIG. 4 depicts an example circuit arrangement with additional details of a stimulation engine that may be implemented in multiple instances in an embodiment of the present patent disclosure.

FIG. 4 depicts a circuit block diagram of an arrangement 400 with additional details of a stimulation engine that may be implemented in multiple instances according to the teachings of the present patent disclosure for purposes of an embodiment consistent with the foregoing arrangement of FIG. 3. A plurality of stimulation engines 402-1 to 402-N are controlled by a digital control logic block 404 and a multi-stim set control block 406 that may be provided in conjunction with or as part of an IMD architecture as discussed above, wherein engines 402-1 to 402-N are substantially analogous to SE modules 306-1 to 306-N of FIG. 3. In one embodiment, each stimulation engine includes a programmable current regulator operative as a current sink circuit, discharge switching circuitry, first switching circuitry configured to switchably connect an anodic node of the stimulation engine to a VM output node operative to supply anodic voltage, and second switching circuitry configured to actuate a switchable coupling between the current sink circuit and a cathodic node of the stimulation engine. Broadly, the digital control logic block 404, which may be implemented as a state machine in some embodiments, and a selector module 408 are operative under appropriate timing control for independently controlling respective stimulation engines 402-1 to 402-N such that each engine may be activated to stimulate a corresponding set of electrodes independently from or in concert with the remaining stimulation engines based on applicable stimulation settings provided to the respective engines 402-1 to 402-N under multi-stim set control 406. As previously noted, multiple electrode sets 412 of an IMD's lead system may be mapped to different output channels 410, which may be driven by respective stimulation engines under selector control of block 408.

By way of example, stimulation engine 402-1 is shown as anodic node 456, cathodic node 458, programmable current sink 422, first switching circuitry 452 operative to switchably couple the anodic node 456 to a VMULT/VM connection node 450 that is driven by a common VM output (not shown in this FIG.), second switching circuitry 434 to actuate switchable coupling between the current sink 422 and cathodic node 458, and passive discharge switching circuitry 472 coupled or otherwise disposed between anodic and cathodic nodes 456, 458. It should be appreciated that various switching circuitry blocks of example engine 402-1 may be implemented using a variety of electronic devices such as transistors, diodes, gates, etc., that may be actuated responsive to appropriately timed digital control signals having suitable logic levels depending on whether the stimulation engine is activated for energizing a select set of electrodes mapped to particular channel(s) (i.e., stimulation mode) or rendered in discharge mode (e.g., in a passive discharge condition where stimulation of a corresponding electrode set is removed).

In one embodiment, the digital control logic block 404 may comprise circuitry to generate a plurality of pulse control signals 405A and discharge control signals 405B for respectively actuating at least a subset of stimulation engines 402-1 to 402-N by generating suitable signals to turn on or off the first and second switching circuitry 452, 434, and passive discharge switching circuitry 472 of the respective stimulation engine depending on whether the stimulation engine is operating in stimulation mode or discharge mode. Further, timing control of the first and second switching circuitry 452, 434 and passive discharge switching circuitry 472 of each respective stimulation engine may be coordinated with the timing of pulse voltage control signals 425 (designated as AMP signals) provided to respective current sink circuitry 422 for achieving synchronized operations of the respective stimulation engine. It should be appreciated that digital control logic block 404 and multi-stim set control block 406 may therefore be configured to provide appropriate switch circuitry control signals 405A/405B and pulse setting signals 407 that are coordinated for respective stimulation engines although such switch circuitry control signals 405A/405B and pulse setting signals 407 may be different for different stimulation engines in terms of logic levels, timing control, amplitude/range levels, and the like, so that each stimulation engine's operations for stimulation and/or discharge of associated electrode sets may be independently controlled. Accordingly, in an example scenario, a portion of stimulation engines may be activated for stimulating corresponding sets of electrodes, another portion of stimulation engines may be disposed in a discharge mode for discharging the electrode sets that may have been previously energized by such stimulation engines, while a yet another portion of stimulation engines may not be connected to any electrodes at all (i.e., in inactive or off state).

As illustrated in FIG. 4, each respective stimulation engine, e.g., engine 402-1, is operative to receive from the digital control logic block 404 a first control signal 454 for controlling first switching circuitry 452, a second control signal 436 for controlling second switching circuitry 434, and a third control signal 474 for controlling the passive discharge switching circuitry 472. Depending on the timing and SE selection control, the first and second control signals 454, 436 may be asserted for a select stimulation engine (e.g., engine 402-1), in a stimulation mode, to enable the first and second switching circuitry 452, 434 of the select stimulation engine 402-1 for respectively connecting the VM output connection node 450 to the anodic node 456 and the current sink circuit 422 to the cathodic node 458 in order to facilitate stimulation of a corresponding select set of the electrodes while the third control signal 474 is de-asserted to disable the passive discharge switching circuitry 472 of the select stimulation engine 422. In similar fashion, the first and second control signals 454, 436 may be de-asserted for a select stimulation engine (e.g., engine 402-1), in a passive discharge mode, to disable the first and second switching circuitry 452, 434 of the select stimulation engine 402-1 for respectively disconnecting the VM output connection node 450 from the anodic node 456 and the current sink circuit 422 from the cathodic node 458 while the third control signal 474 is asserted to enable the passive discharge switching circuitry 472 of the select stimulation engine 402-1 for facilitating discharge (e.g., passive discharge) of a corresponding select set of the electrodes.

Skilled artisans will appreciate that logic levels associated with assertion/de-assertion of the various control signals provided in the embodiment of FIG. 4 may be dependent on the type of boolean logic used relative to the digital electronic devices, transistors, gates, etc., comprising the corresponding switching circuitry respectively actuated thereby. Further, because of the timing synchronization and/or complementary nature of the digital logic involved, control signals 454, 436 (which may be cumulatively referred to as PULSE[1:N] or PLS[1:N] signals with respect to N stimulation engines 402-1 to 402-N) and/or passive discharge control signal 474 (which may be cumulatively referred to as DIS[1:N] signal with respect to N stimulation engines 402-1 to 402-N) may be derived or generated from one another or from one or more signals provided to or from the digital control logic block 404 by different portions of an IMD and/or associated external programmer device.

Because VM output node connectivity in each stimulation engine is switched independently depending on the selected electrode set configuration, in addition to the discharge switching functionality also being provided on a per-engine basis, an example implementation of the embodiment shown in FIG. 4 advantageously allows the stimulation engines to share electrodes or be kept completely independent based on the desired therapy. Additionally, multiple stimulation engines may be configured to provide independent therapy to as many target areas in the patient and/or to provide complex stimulation waveforms by means of delivering multi-frequency pulsing signals to the same area that may be designed to interact/interfere with one another in desirable patterns.

In one example implementation, current sink circuit 422 of example engine 402-1 may include a digital-to-analog converter (DAC) 426 interfacing with appropriate pulse voltage control signal 425 (e.g., having suitable magnitude and polarity depending on the type of stimulation current being programmed) to generate a digitally-programmed analog voltage level as an output signal that may be provided to an error amplifier 424. In one arrangement, the error amplifier 424 may be implemented as an op amp having two inputs for providing a differential input and operative with a power supply rail voltage VDDA and ground 432 that may be commonly tied to an IMD battery ground along with other ground nodes of remaining stimulation engines. Accordingly, the digitally-programmed analog voltage signal (VDAC) output may be coupled to a first input of the error amplifier 424, wherein a second input is coupled to a programmable resistor network 428 operative to provide a digitally-programmed resistance (RSCALE) in a feedback loop arrangement for modulating a current sink output. In general operation, the error amplifier 424 may be programmatically configured to generate a desired amount of stimulation current ($I_{STIM}$), which may be set by the application of Ohm's Law in view of the digitally-programmed resistance RSCALE, where $I_{STIM}$=(VDAC/RSCALE), at a node 431 to which the programmable resistor network 428 is connected. A current conducting device 430 actuated by the output of error amplifier 424 may be coupled to the node 431 for facilitating the stimulation current $I_{STIM}$ flowing through one or more electrodes (i.e., a particular electrode set) when the select stimulation engine, e.g., engine 402-1, is in stimulation mode wherein cathodic node 458 of the select stimulation engine is connected to one side of the selected electrode set and anodic node 456 of the select stimulation engine coupled to the associated electrodes across the ETI interface is connected to the VM output connection node 450 under suitable control signal logic as described above. It should be appreciated that active discharge in an example embodiment may be attained by a stimulation engine by delivering a constant current pulse to the electrodes in a reverse current flow direction—namely, it is achieved by respectively swapping the connectivity of the electrodes programmed as anodes and cathodes via selector block 408 while delivering a constant current pulse with an appropriate VM setting and parameter settings for electrode discharge (e.g., amplitude and pulse width), which may be the same or different than the settings used during stimulation.

Figures 5A, 5B:
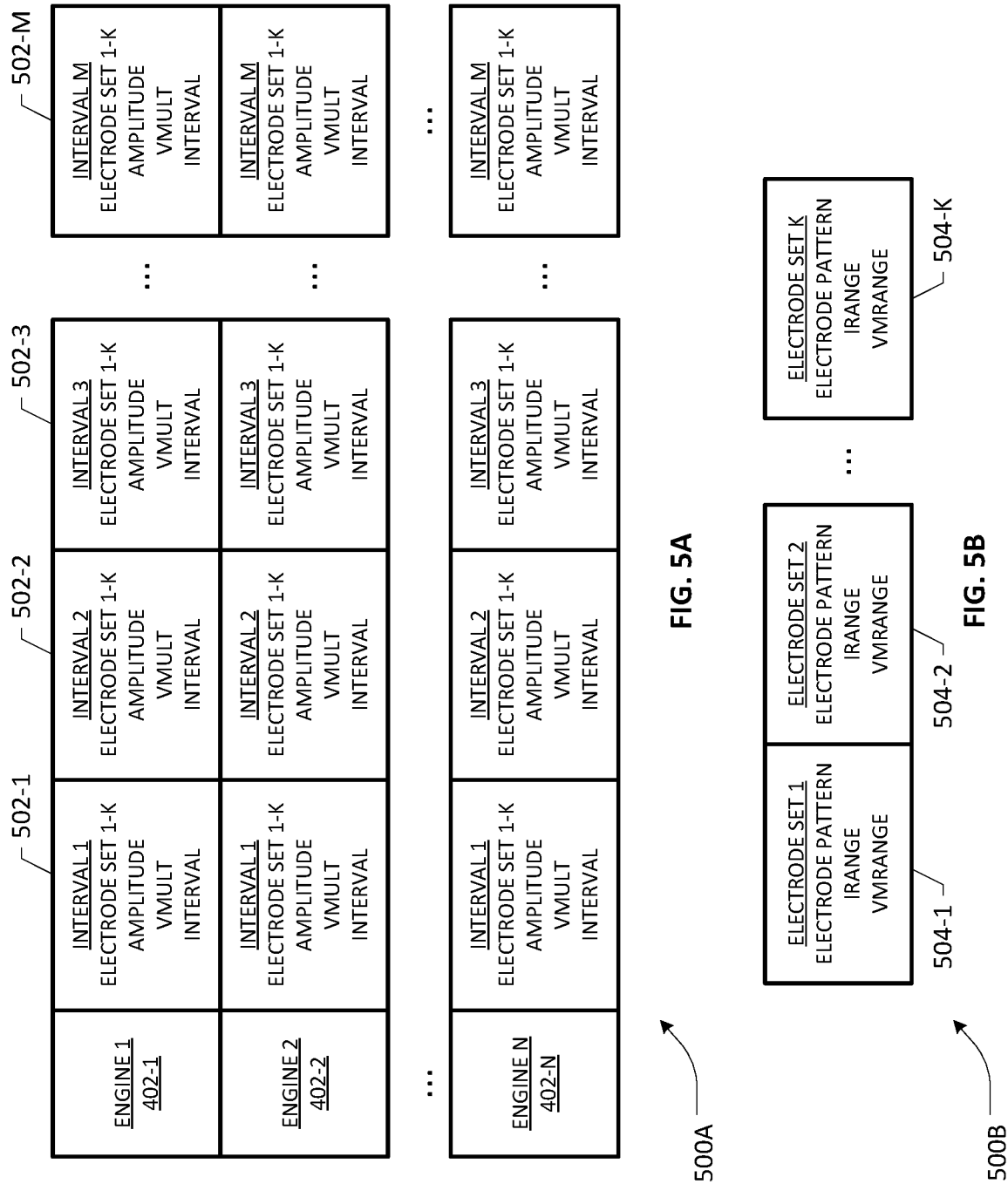
FIGS. 5A and 5B depict example stimulation settings and combination of electrode sets with respect to different stimulation engines in an illustrative scenario according to an implementation of the present patent disclosure.

FIGS. 5A and 5B depict example stimulation settings and one or more combinations of electrode sets with respect to different stimulation engines in an illustrative scenario according to an implementation of the present patent disclosure. Table 500A of FIG. 5A illustrates engines 402-1 to 402-N, each configurable to provide different stimulation settings 502-1 to 502-M over a plurality of time intervals, wherein each setting may correspond to a particular electrode set (e.g., sets 1 to K, each comprising a particular combination selected from the total number of electrodes of a lead system), pulse amplitude, VM voltage level as well as a corresponding time duration, among others. It should be noted that different stimulation engines may have different settings in respect of any of the parameters thereof. Table 500B of FIG. 5B is illustrative of different electrode patterns and associated electrical parametric ranges, collectively referred to by reference numerals 504-1 to 504-K, corresponding to respective electrode sets (K).

Figure 6:
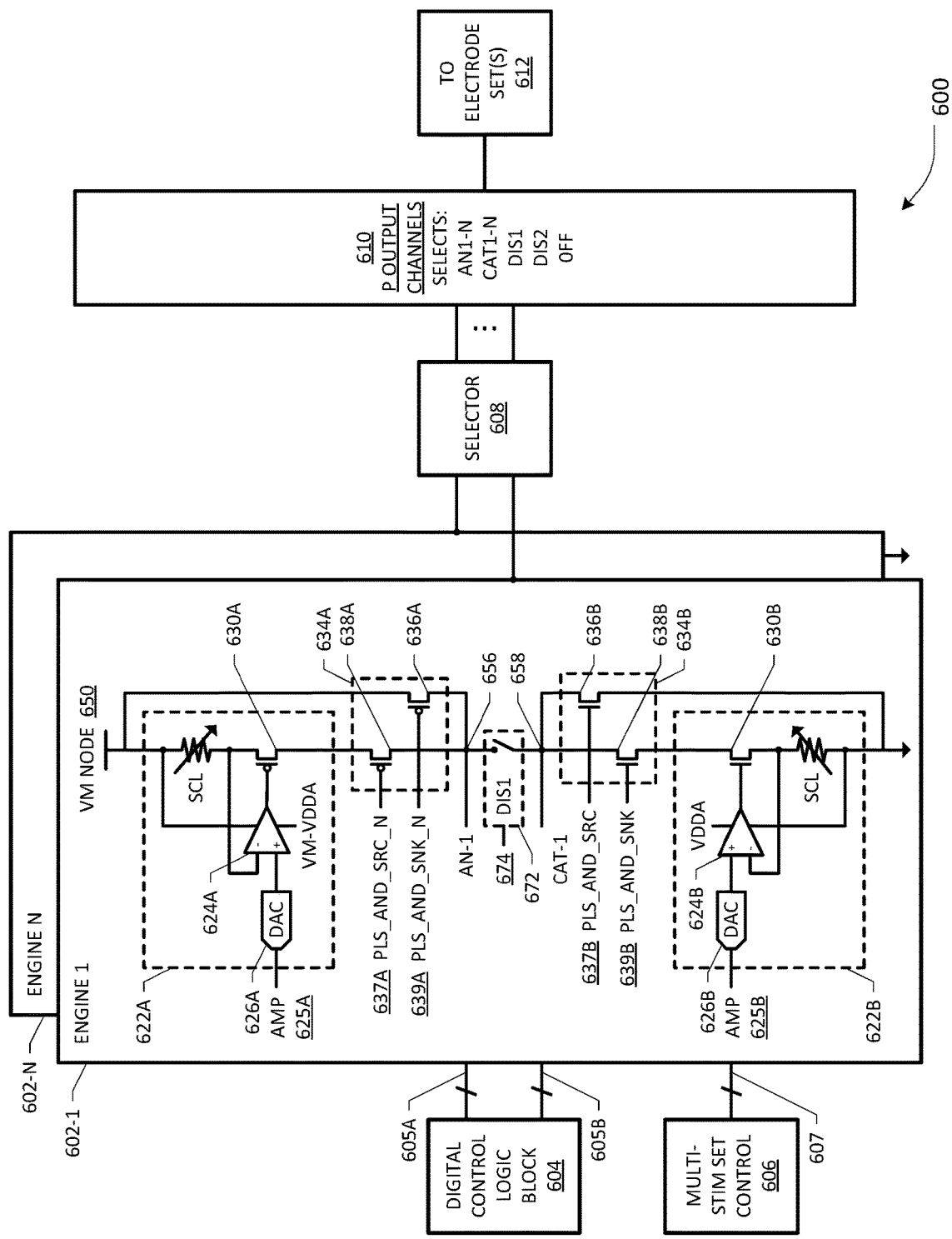
FIG. 6 depicts an example circuit arrangement with additional details of a stimulation engine that may be implemented in multiple instances in another embodiment of the present patent disclosure arranged to provide further stimulation selection and discharge flexibility.

FIG. 6 depicts a circuit block diagram of an arrangement 600 with additional details of a stimulation engine that may be implemented in multiple instances according to another embodiment of the present patent disclosure arranged to provide further stimulation selection and discharge flexibility. Essentially, an example stimulation engine of circuit arrangement 600 may be configured in one embodiment to include an additional current regulator circuit operative as a current source that is a mirror replica of a current sink, wherein both the current source and current sink circuits are switchably coupled to respective anodic and cathodic nodes under suitable digital control signaling for stimulation of a select electrode set. By providing a mirrored pair of current regulators, an example stimulation engine may be configured to reverse the polarity of the anodic and cathodic nodes to facilitate active discharging of the select electrode set in a discharge mode to provide additional discharge flexibility that would not be feasible otherwise in the embodiment of FIG. 4 described above. Apart from the added functionality in the digital control logic required to control the switchable connectivity of the current source and sink circuits in both stimulation and active discharge modes as well as additional components in the respective first and switching circuitry blocks, the overall structure of the circuit arrangement 600 is substantially identical to that of the circuit arrangement 400. Because the detailed description provided above with respect to FIG. 4 is generally applicable, *Mutatis mutandis*, to the circuit arrangement 600 of FIG. 6 also, only select features of the circuit arrangement 600 will be set forth below.

As before, a plurality of stimulation engines 602-1 to 602-N may be provided that are selectably operative to stimulate or discharge corresponding sets of electrodes in independent manner based on selector control and applicable multi-stim set control. Each stimulation engine, e.g., engine 602-1, includes a current source circuit 622A and a current sink circuit 622B, which are switchably connectable to nodes 656, 658, respectively, via switching circuitry 634A and switching circuitry 634B, wherein the nodes can be configured to operate as anodic and cathodic nodes for electrode set stimulation in one implementation. Similar to the circuit arrangement 400 of FIG. 4, passive discharge switching circuitry 672 may be coupled or otherwise disposed between nodes 658 and 656, which may be selectively activated in a passive discharge mode of operation. A digital control logic block 604 is configured to provide appropriate switching circuitry control signals 605A and discharge switching control signals 605B to respective stimulation engines 602-1 to 602-N. Current sink circuit 622B, which is substantially identical to current sink circuit 422 of the circuit arrangement 400, as well as mirroring current source circuit 622A are operative in response to appropriate pulse setting signals 607 provided by multi-stim set control block 606. Because of the complementary nature of the operation of current source/sink circuits 622A, 622B, respective signals, i.e., AMP 625A and AMP 625B, provided to DAC 626A and DAC 626B of current source/sink circuits 622A, 622B, may have complementary voltage polarity levels also. Further, power supply rails of respective error amplifiers 624A, 624B of current source/sink circuits 622A, 622B may also be biased accordingly. Similar to current sink circuit 422 of the circuit arrangement 400, a power rail of error amplifier 624B of current sink circuit 622B is coupled to a ground commonly coupled to the IMD battery's ground. On the other hand, a power rail of error amplifier 624A of current source circuit 622A is coupled to the VM connection node 650, which is commonly coupled to the output node of a common VM (e.g., output node 304 of VMULT 302 shown in FIG. 3) as noted above.

In respect of example stimulation engine 602-1, comparing with the circuit arrangement 400 of FIG. 4, switching circuitry 634B is roughly analogous to second switching circuitry 434 while switching circuitry 634A is roughly analogous to first switching circuitry 452. A first pair of control signals 637A, 639A (designated as PLS_AND_SRC_N and PLS_AND_SNK_N, respectively) are operative for controlling switching circuitry 634A and a second pair of control signals 637B, 639B (designated as PLS_AND_SRC and PLS_AND_SNK, respectively) are operative for controlling switching circuitry 634B of example engine 602-1. Taken cumulatively, all such pairs of control signals corresponding to respective stimulation engines of the circuit arrangement 600 form switching circuitry control signals 605A provided by the digital control logic block 604. With respect to discharge switching circuitry 672 disposed between nodes 658 and 656 of example engine 602-1, a passive discharge control signal 674 is analogous to third control signal 474 of the circuit arrangement 400, which may be asserted when example engine 602-1 is disposed in a passive discharge mode. Collectively, such discharge control signals 674 corresponding to respective stimulation engines form discharge switching control signals 605B provided by the digital control logic block 604, which may be independently asserted with respect to particular stimulation engines selected for discharging corresponding electrode sets according to the applicable discharge parameters (e.g., discharge pulse voltage levels, timing intervals, etc.). Additional details regarding selection of discharging parameters and configuration of electrodes for discharging, including adaptive active discharging, may be found in the '643 patent application publication incorporated by reference hereinabove.

In general, switching circuitry 634A and 634B of the circuit arrangement 600 may be formed using a variety of electronic devices, components, diodes, gates, transistors, etc., for facilitating switchable/configurable connectivity between VM node 650 and node 656 via the current source circuit 622A and between the current sink circuit 622B and node 658, each having a corresponding conductive device 630A, 630B, respectively driven by associated error amplifiers 624A and 624B, with respect to stimulation and active discharge operations in conjunction or coordination with suitable timing control, stim set control, active discharge pulse control, and active discharge switching circuitry control. In one embodiment, switching circuitry 634B comprises a pair of n-channel MOSFET (NMOS) devices 638B, 636B, whose gates are driven by PLS_AND_SNK signal 639B and PLS_AND_SRC signal 637B, respectively. In a complementary fashion, switching circuitry 634A comprises a pair of p-channel MOSFET (PMOS) devices 638A, 636A, whose gates are driven by PLS_AND_SRC_N signal 637A and PLS_AND_SNK_N signal 639A, respectively.

In general operation, a first pair of control signals for controlling the first switching circuitry, e.g., circuitry 634A, a second pair of control signals for controlling the second switching circuitry, e.g., circuitry 634B, are generated such that the second pair of control signals have complementary logic levels with respect to the first pair of control signals. For example, with respect to a select stimulation engine, e.g., engine 602-1, that is rendered in a stimulation mode, the first pair of control signals 637A, 639A and the second pair of control signals 637B, 639B may be asserted with suitable respective first logic levels (that may be complementary with respect to each other), to enable the first and second switching circuitry 634A, 634B of the select stimulation engine 602-1 for respectively connecting the VM output node 650 to the anodic node 656 and the current sink circuit 622A to the cathodic node 658 in order to facilitate stimulation of a corresponding select set of the electrodes, while a third control signal, e.g., passive discharge control signal 674, is de-asserted to disable the passive discharge switching circuitry 672 of the select stimulation engine 602-1. In similar fashion, the first pair of control signals 637A, 639A and the second pair of control signals 637B, 639B are de-asserted with suitable respective second logic levels (that may be complementary with respect to each other) for the select stimulation engine 602-1 in a discharge mode to disable the first and second switching circuitry 634A, 634B of the select stimulation engine 602-1, respectively, while the third control signal, e.g., passive discharge control signal 674, is asserted to enable the passive discharge switching circuitry 672 of the select stimulation engine 602-1 for facilitating passive discharge of the corresponding select set of the electrodes that may have been previously energized to provide stimulation therapy. Again, it should be noted that active discharge may be attained by a stimulation engine by delivering a constant current pulse to the electrodes in a reverse current flow direction—namely, it is achieved by respectively swapping the connectivity of the electrodes programmed as anodes and cathodes via selector block 608 while delivering a constant current pulse with an appropriate VM setting and parameter settings for electrode discharge (e.g. amplitude and pulse width), which may be the same or different than the settings used during stimulation, as previously noted.

Similar to the operation of the circuit arrangement 400 described above, logic levels associated with assertion/de-assertion of the various control signals provided in the embodiment of FIG. 6 may be dependent on the type of boolean logic used relative to the digital electronic devices, transistors, gates, etc., forming the corresponding switching circuitry respectively actuated thereby. Also, one or more control signals may be derived or generated from one another or from control signals provided to or from the digital control logic block 604 by different portions of an IMD and/or associated external programmer device. Additionally, the digital control logic block 604 (which may be implemented as a state machine in some embodiments) and selector module 608 are operative under appropriate timing control for independently controlling respective stimulation engines 602-1 to 602-N such that each engine may be activated to stimulate a corresponding set of electrodes independently from or in concert with the remaining stimulation engines based on applicable stimulation settings provided to the respective engines 602-1 to 602-N under multi-stim set control 606. Accordingly, multiple electrode sets 612 of an IMD's lead system may be mapped to different output channels 610, which may be driven by respective stimulation engines under selector control of block 608, similar to the embodiment of FIG. 4.

It should be further appreciated that various example stimulation settings and electrode set combinations with respect to different stimulation engines in an illustrative scenario set forth in FIGS. 5A and 5B may also be applied in one implementation of the circuit arrangement of FIG. 6, wherein a plurality of discharge settings and parameters (e.g., comprising discharge programs DIS-1 to DIS-M) may be additionally included with respect to discharge cycling of select electrode sets in accordance with the teachings herein. In still further arrangements, switching circuitry for switchably coupling the current sink circuit of an example stimulation engine to its cathodic node may be configured primarily to control and maintain suitable timing relationships in relation to the operations of coupling the switchable VM node to the engine's anodic node and/or providing AMP pulsing to the current sink circuit according to a stimulation setting. In such arrangements, by appropriately timing or triggering the connection between the VM node and the engine's anodic node based on how the AMP pulsing is provided to the current sink circuit, the switching circuitry for coupling the current sink circuit to the engine's cathodic node may be dispensed with in one implementation of either circuit arrangements 400, 600 described above.

Figure 7:
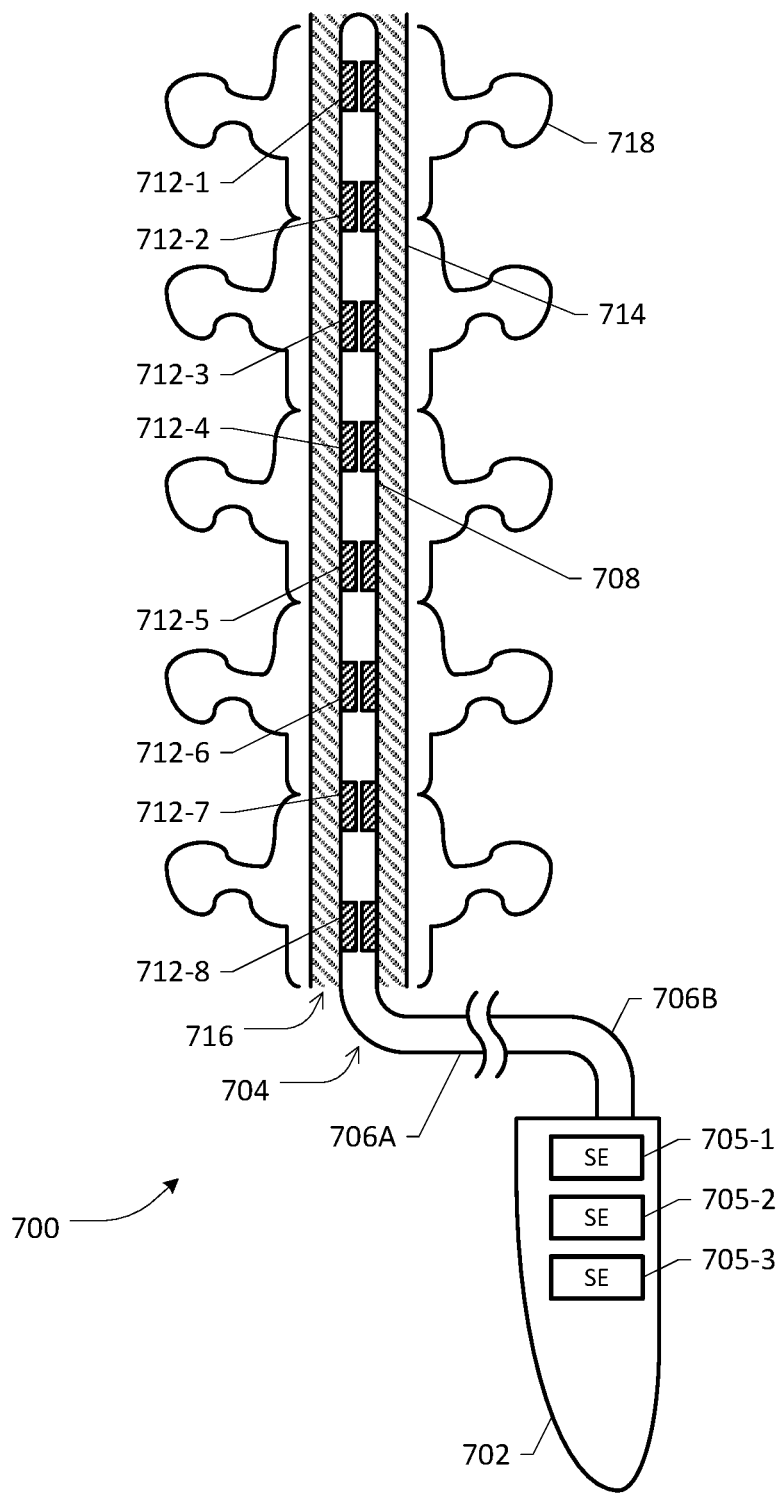
FIG. 7 illustrates an example spinal cord stimulation (SCS) therapy application involving an IMD with multiple stimulation engines and associated lead system having a plurality of electrodes that may be stimulated using multiple stimulation sets without channel collision according to an embodiment of the present disclosure.

FIG. 7 illustrates an example spinal cord stimulation (SCS) therapy application 700 involving a pulse generator or IMD 702 and associated lead system 704 having a plurality of electrodes 712-1 to 712-8 wherein different groupings of electrodes may be simultaneously and independently energized pursuant to respective stimset programs during a stimulation therapy according to an embodiment of the present disclosure. Preferably, the lead system 704 comprises a lead body 706A/B coupled to an implantable lead 708 that may be positioned at a desired target position in an epidural space 716 defined by a plurality of vertebrae of a patient so as to be in close proximity to a nerve tissue of interest, e.g., a spinal cord 714. Example implantable lead 708 includes eight electrodes 712-1 to 712-8, which may comprise ring electrodes, segmented or split electrodes, and the like that may be separated from one another by equal or unequal portions of encapsulating material. The implantable lead 708 is connected via lead body 706A/706B to IPG/IMD 702 that includes at least an embodiment of an MSE module of the present disclosure that may be configured to be operative with suitable diagnostic circuitry and/or programming devices. By way of example, three SEs 705-1, 705-2, 705-3 are shown, which may be selectively and independently configured to provide different combinations of stimulation therapy to electrodes 712-1 to 712-8. Illustratively, SE 705-1 may be activated to stimulate electrodes 712-1 to 712-4 and SE 705-2 may be activated stimulate electrodes 712-5 to 712-8, while SE 705-3 may be inactive. Accordingly, electrodes 712-1 to 712-4 and electrodes 712-5 to 712-8 may be energized, i.e., stimulated, e.g., with appropriate constant current pulses, wherein the individual stimulation currents drawn via respective loads may be optimized based on respective SE control as previously described.

Figure 8:
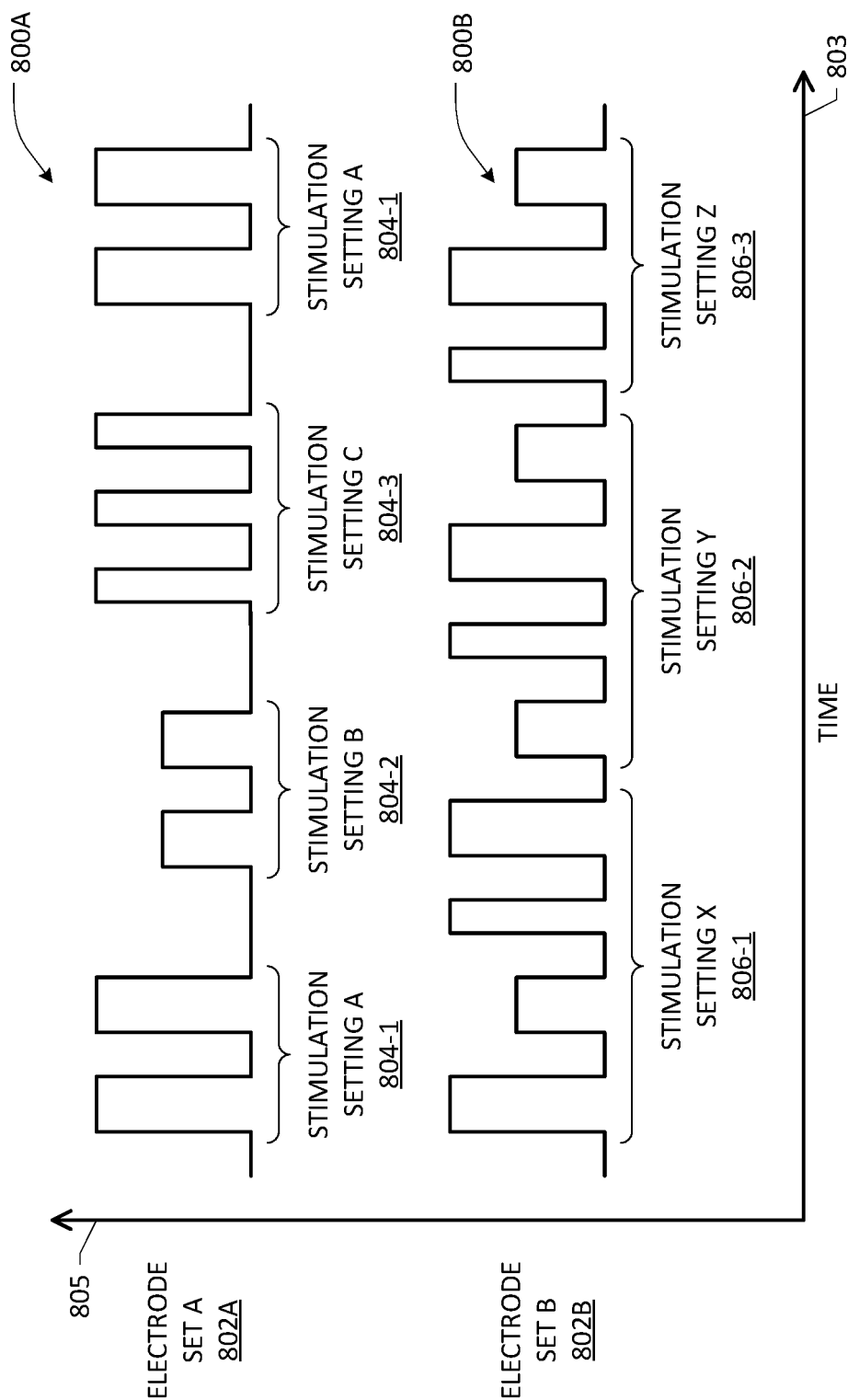
FIG. 8 depicts a panel of illustrative waveforms associated with stimulation therapies applied to two sets of electrodes according to some embodiments of the present disclosure.

FIG. 8 depicts a panel of illustrative waveforms associated with stimulation therapies applied to two sets of electrodes according to some embodiments of the present disclosure. Panels 800A and 800B exemplify stimulation waveforms respectively associated with two electrode sets 802A 802B, each energized by a respective stimulation engine, wherein an electrical parameter (e.g., current amplitude) and time are plotted on Y-axis 805 and X-axis 803, respectively, as shown. Waveform panel 800A is illustrated as a plurality of stimulation settings 804-1 to 804-3 that are applied successively over time to electrode set A 802A. Likewise, waveform panel 800B is illustrative of a plurality of stimulation settings 806-1 to 806-3 applied to electrode set B 802B. Although both waveforms overlap over temporally, there is no unintended stimulation during collisions because of the common VM voltage, independent stimulation timing control and current regulation provided in accordance with the teachings herein.

Figure 9:
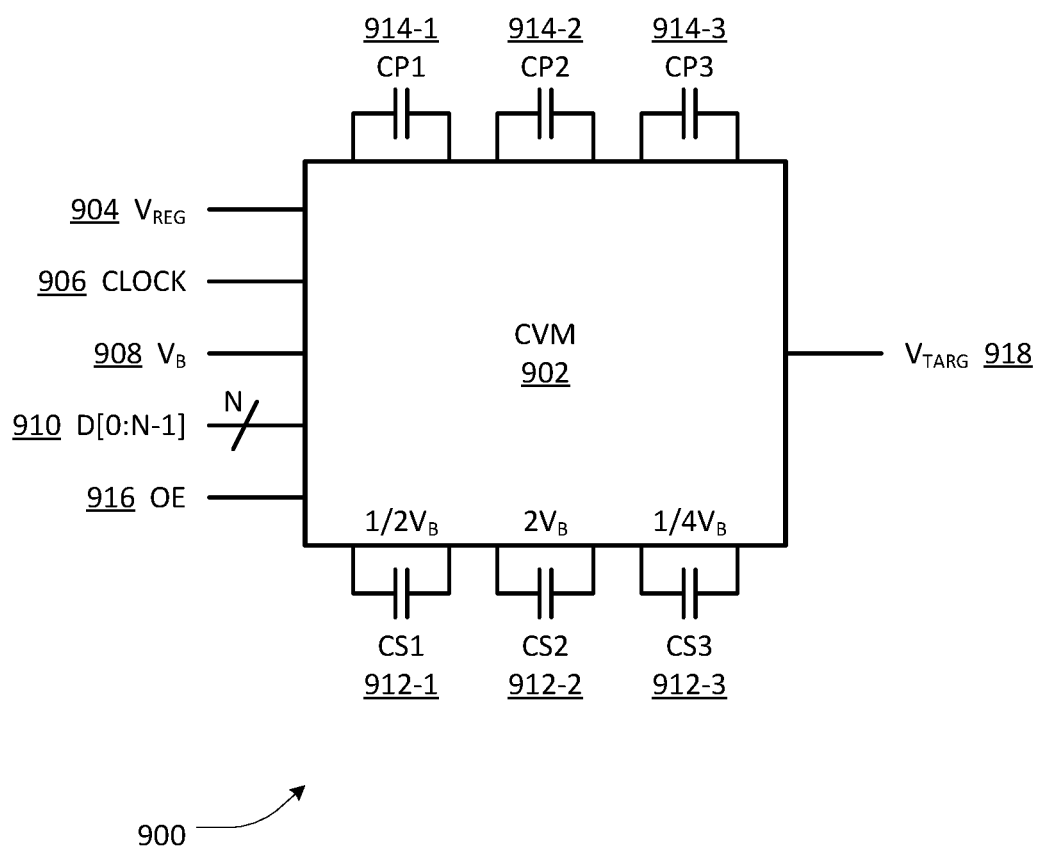
FIG. 9 depicts a high level block diagram of an adjustable voltage multiplier that may be used in an embodiment of the present disclosure.

FIG. 9 depicts a high level block diagram of an adjustable voltage multiplier that may be used in a switchable connection arrangement with one or more stimulation engines according to an embodiment of the circuit arrangements of FIGS. 3, 4 and/or 6 set forth above for purposes of the present disclosure. By way of illustration, voltage multiplier 900 may be configured as an adjustable charge pump arrangement operative to generate a target voltage at an output node for purposes of an example embodiment herein. Generally, a representative embodiment of voltage multiplier configuration 900 may be arranged to support power supply voltage multiplier and/or divider elements in a binary ladder distribution to provide a desired number of output voltage steps using a circuit design which may readily be implemented in a single integrated circuit (IC) or multiple ICs. For example, a capacitive voltage multiplier (CVM) provided according to a representative embodiment may be operative as a DC-to-DC voltage conversion system comprising a voltage doubler generating twice the battery voltage, the battery itself generating the battery voltage, a voltage halver generating half of the battery voltage, and a voltage quarterer generating a quarter of the battery voltage, and/or any other fractional/multiples thereof. Accordingly, circuitry of an example voltage multiplier configuration may preferably operate to combine the different voltages to provide a range of output voltages in multiple steps, e.g., one-quarter battery voltage (¼ $V_{BATT}$ or $V_B$), or other power source voltage steps. By using such different sources in various combinations and/or by "stacking" these different sources in various ways, the voltage multiplier circuit may be used to provide desired voltages over a suitable range. For example, the output voltage of such a voltage multiplier may range from ¼ $V_B$ to 3¾ $V_B$, in one-quarter battery voltage steps in an example implementation.

In FIG. 9, configuration 900 of the illustrated embodiment includes CVM circuitry block 902 implemented as an IC or other monolithic chip device, a first plurality of pump capacitors CP1 914-1, CP2 914-2, and CP3 914-3, and a second plurality of storage capacitors CS1 912-1, CS2 912-2, and CS3 912-3. CVM 902 is preferably operative responsive to signal inputs VREG 904, CLOCK 906, $V_B$ 908, an N-bit control signal 910, (e.g., a 4-bit signal that may be generated, controlled and/or otherwise configured by a suitable digital control block) and an output enable (OE) signal 916, in order to generate a target output voltage ($V_{TARG}$) at an output node or pin 918 that may be switchably connected to one or more stimulation engines as described above.

VREG 904 of the illustrated embodiment provides a regulated voltage input for use by circuits (e.g., digital control circuits) of CVM 902 in providing voltage multiplication. In an example implementation, VREG 904 is typically at a logic level (e.g., 2.2 volts) that is lower than the power supply voltage (e.g., $V_B$ 908). CLOCK 906 is a system clock signal used for synchronizing operation of aspects of CVM 902 with operation of aspects of a host system (e.g., IMD/IPG of a biostimulation system), such as for digital communication, voltage output timing, etc. $V_B$ 908 provides a power supply voltage level input for use in voltage fractional multiplication by CVM 902. For example, $V_B$ 908 may provide unregulated battery voltage input, such as 4.1 volts where a lithium-ion battery is used. Digital control 910 provides a suitable digital input signal, which may be used in the illustrated embodiment for selecting a desired output voltage level, e.g., depending on stimulation therapy application. OE 916 is operative to selectively enable the output voltage ($V_{TARG}$) at output node 918. Accordingly, an input signal provided at OE 916 may comprise a binary logic level signal which may be asserted at appropriate times (e.g., depending on the CLOCK signal 906).

Pump capacitors CP1 914-1, CP2 914-2, and CP3 914-3 of the illustrated embodiment may be utilized in a voltage generation cycle. Because of the use of a partitioned circuit configuration of CVM 902 of a representative embodiment (and due to the relatively low voltages experienced by capacitors CP1 914-1, CP2 914-2, and CP3 914-3 in an example implementation), the pump capacitors may be relatively small, such as on the order of 0.5 μF. One or more storage capacitors CS1 912-1, CS2 912-2, and CS3 912-3 may be configurably stacked in providing a desired output voltage ($V_{TARG}$). Moreover, in order to sustain a relatively constant (i.e., flat) output voltage level during a voltage output cycle, storage capacitors CS1 912-1, CS2 912-2, and CS3 912-3 may be larger than the pump capacitors, such as on the order of 100 μF. Accordingly, various capacitors utilized in generating a particular voltage multiple or voltage fraction need not be matched in implementing a particular charge pump arrangement of CVM 902. For example, according to a representative embodiment where pump capacitors are used in combination with storage capacitors to generate a voltage multiple or voltage fraction, the capacitors are not necessarily matched.

It should be appreciated that through controlled stacking of the various storage capacitors in providing a desired output voltage, the maximum voltage levels experienced by particular capacitors (and other components) may be minimized. Therefore, one or more of the capacitors or other circuitry may be sized differently with respect to one another according to some embodiments. Accordingly, various ones of the pump capacitors may be sized differently with respect to other pump capacitors and/or various ones of the storage capacitors may be sized differently with respect to other storage capacitors. Skilled artisans will therefore recognize that various charge pump capacitor configurations may be implemented in additional or alternative embodiments for purposes of the present patent disclosure.

In operation according to a representative embodiment, CVM 902 provides selectable voltage output at $V_{TARG}$ node 918 in various increments, e.g., from $0V_B$ to 3% $V_B$ in ¼ $V_B$ steps. In one implementation, a logic low input at OE 916 may be used to turn the voltage output at $V_{TARG}$ node 918 off (i.e., 0 $V_B$), such as during a voltage generation or refresh cycle. A logic high input at OE 916 in combination with a particular N-bit combination logic input at terminal 910 may be used to turn the voltage output at $V_{TARG}$ node 918 on and select a particular voltage level from ¼ $V_B$ to 3¾ $V_B$ by appropriately configuring at least a portion of the charge pump capacitors. Other fractional voltages may be provided through the use of combinations of capacitors different than those of the exemplary embodiment shown in FIG. 9.

Generation of voltages using a voltage multiplier/conversion circuit such as the representative circuit 900 shown in FIG. 9 may include a plurality of phases, wherein an output of the voltage multiplier/conversion circuit may be disabled during one or more such phases. For example, a charge phase may be used to charge the pump capacitors with current from the power supply and a pump phase may be used to pump the charge into storage capacitors (the combination of these phases being referred to as a generation phase). A source phase may be used to output a desired voltage using an appropriate configuration of pump capacitors and/or storage capacitors (i.e., charge pump capacitors) based on the control logic 910. Additional details regarding example interconnection or configuration of pump and storage capacitors in a charge phase and a pump phase, as well as selection of different output voltages ($V_{TARG}$) using appropriate selection circuitry operating under suitable digital control may be found in U.S. Pat. No. 8,446,212, entitled "PULSE GENERATOR HAVING AN EFFICIENT FRACTIONAL VOLTAGE CONVERTER AND METHOD OF USE", which is incorporated herein by reference.

Figure 10A:
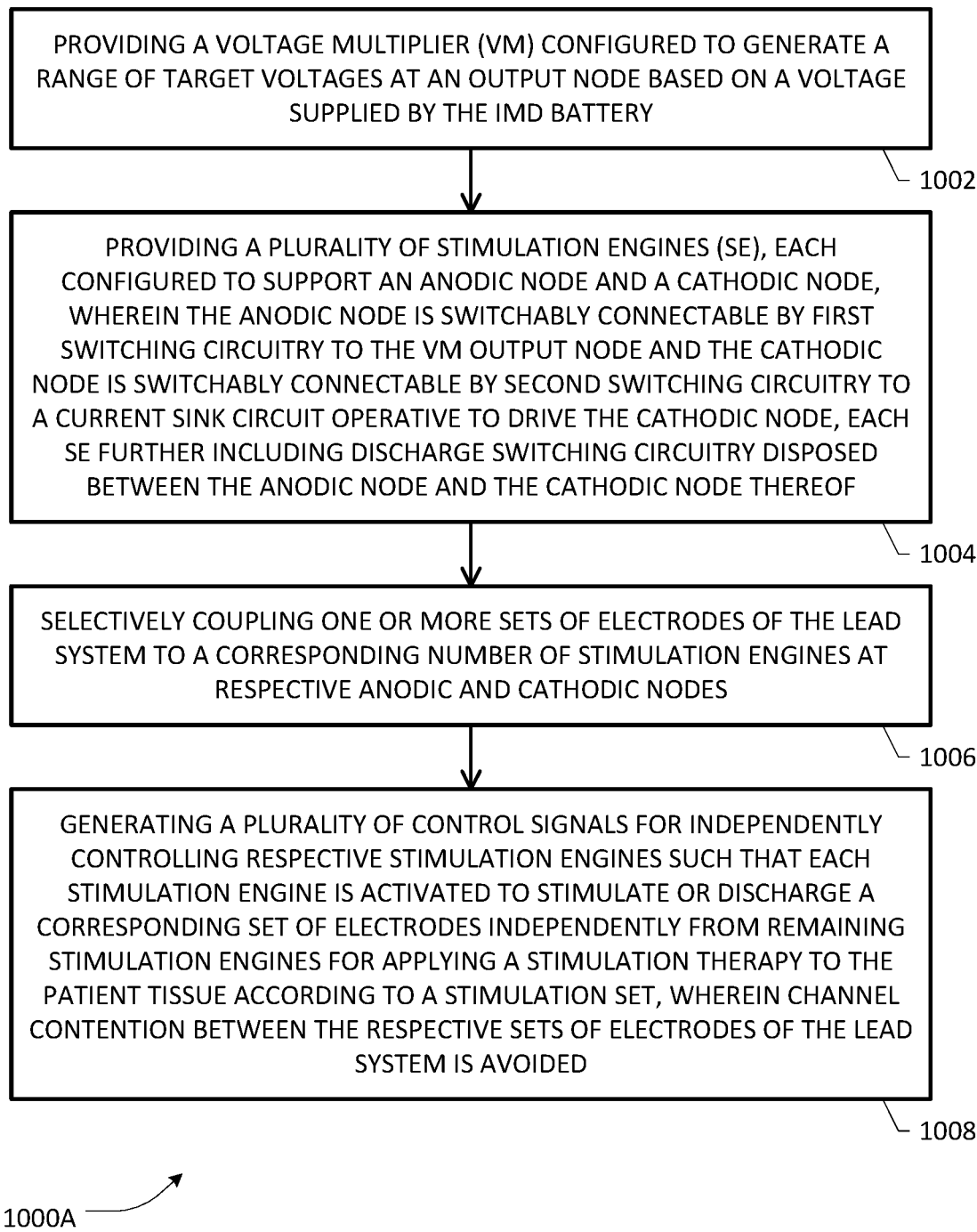

FIGS. 10A-10C depict flowcharts of blocks, steps and/or acts that may be (re)combined in one or more arrangements for facilitating a stimulation therapy method with multiple stimulation engines of a biostimulation system according to some embodiments of the present disclosure. Example process 1000A of FIG. 10A commences with providing a voltage multiplier (VM) configured to generate a range of target voltages at an output node (i.e., VM output node) based on a battery voltage supplied by the IMD of the biostimulation system (block 1002). At block 1004, a plurality of stimulation engines (SE) are provided, each configured to support an anodic node and a cathodic node, wherein the anodic node is switchably connectable by first switching circuitry to the VM output node and the cathodic node is switchably connectable by second switching circuitry to a current sink circuit operative to drive the cathodic node, each SE further including discharge switching circuitry disposed between the anodic node and the cathodic node thereof. At block 1006, one or more sets of electrodes of the biostimulation system are selectively coupled to a corresponding number of SEs at respective anodic and cathodic nodes. At block 1008, a plurality of control signals are generated for independently controlling respective stimulation engines such that each stimulation engine is activated to stimulate or discharge a corresponding set of electrodes independently from remaining stimulation engines for applying a stimulation therapy to the patient tissue according to a stimulation set, wherein channel contention between the respective sets of electrodes of the lead system is avoided. In one variation, example process 1000B depicted in FIG. 10B may involve generating, for each respective stimulation engine, a first control signal for controlling the first switching circuitry, a second control signal for controlling the second switching circuitry and a third control signal for controlling the discharge circuitry of the respective stimulation engine, as set forth at block 1022. Another variation as set forth in example process 1000C of FIG. 10C may involve providing, for each stimulation engine, a current source circuit, wherein the first switching circuitry is arranged to switchably connect the anodic node of the stimulation engine to the VM output node via the current source circuit (block 1032). In such an arrangement, process 1000C further includes generating, for each respective stimulation engine, a first pair of control signals for controlling the first switching circuitry, a second pair of control signals for controlling the second switching circuitry, the second pair of control signals having complementary logic levels with respect to the first pair of control signals, and a third control signal for controlling the discharge circuitry of the respective stimulation engine (block 1034).

Figure 11A:
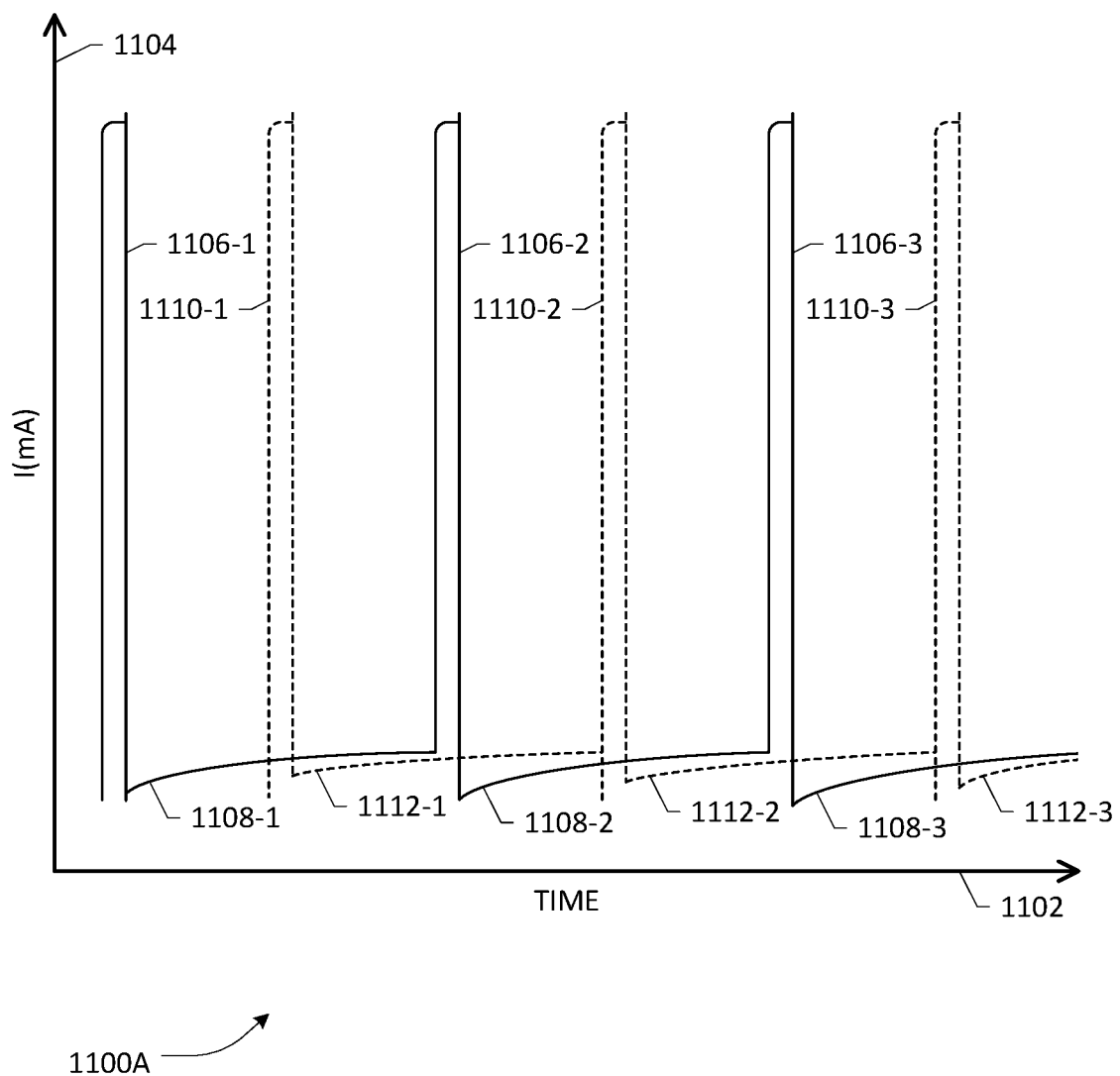
FIGS. 11A-11C each depict a panel of waveform simulations associated with stimulation therapies provided by two stimulation engines according to some embodiments of the present disclosure.
Figure 11B:
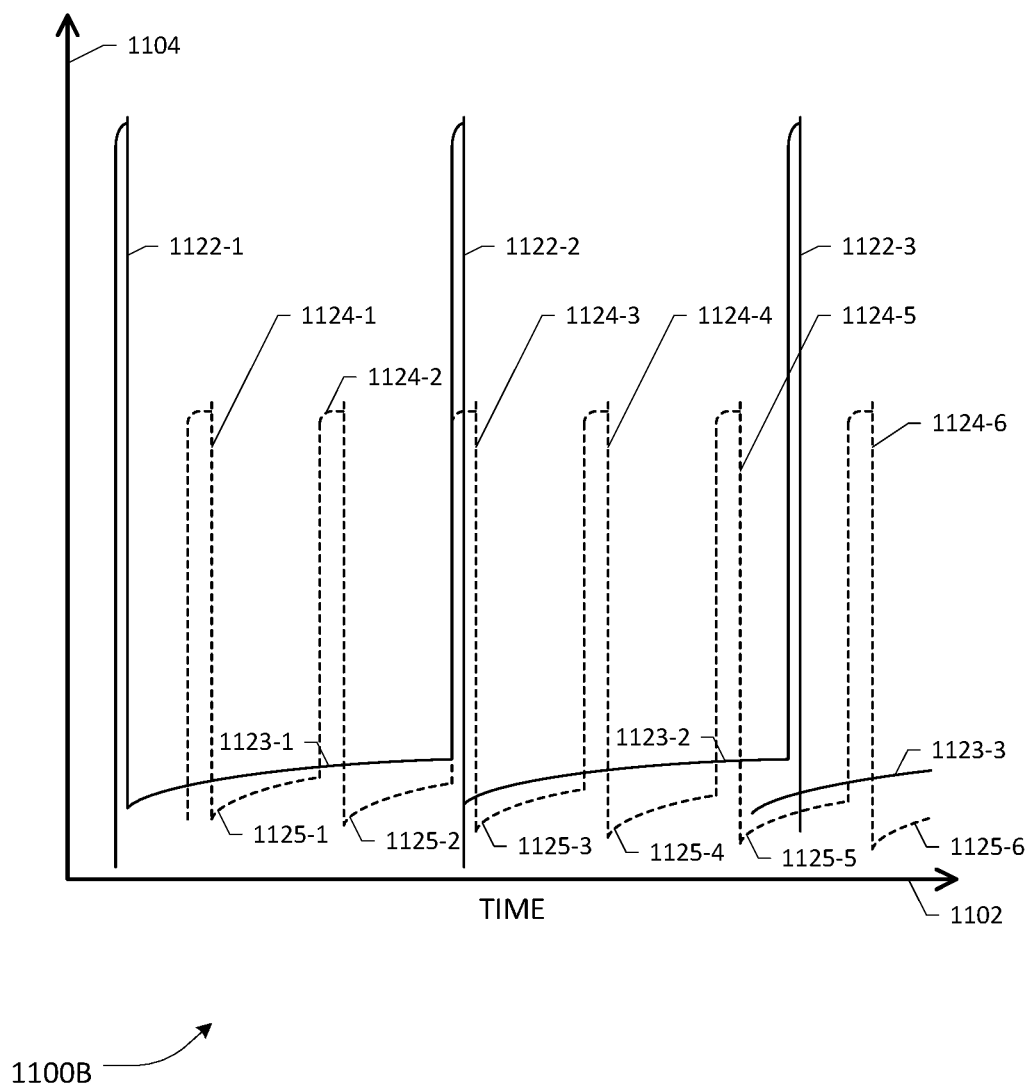
Figure 11C:
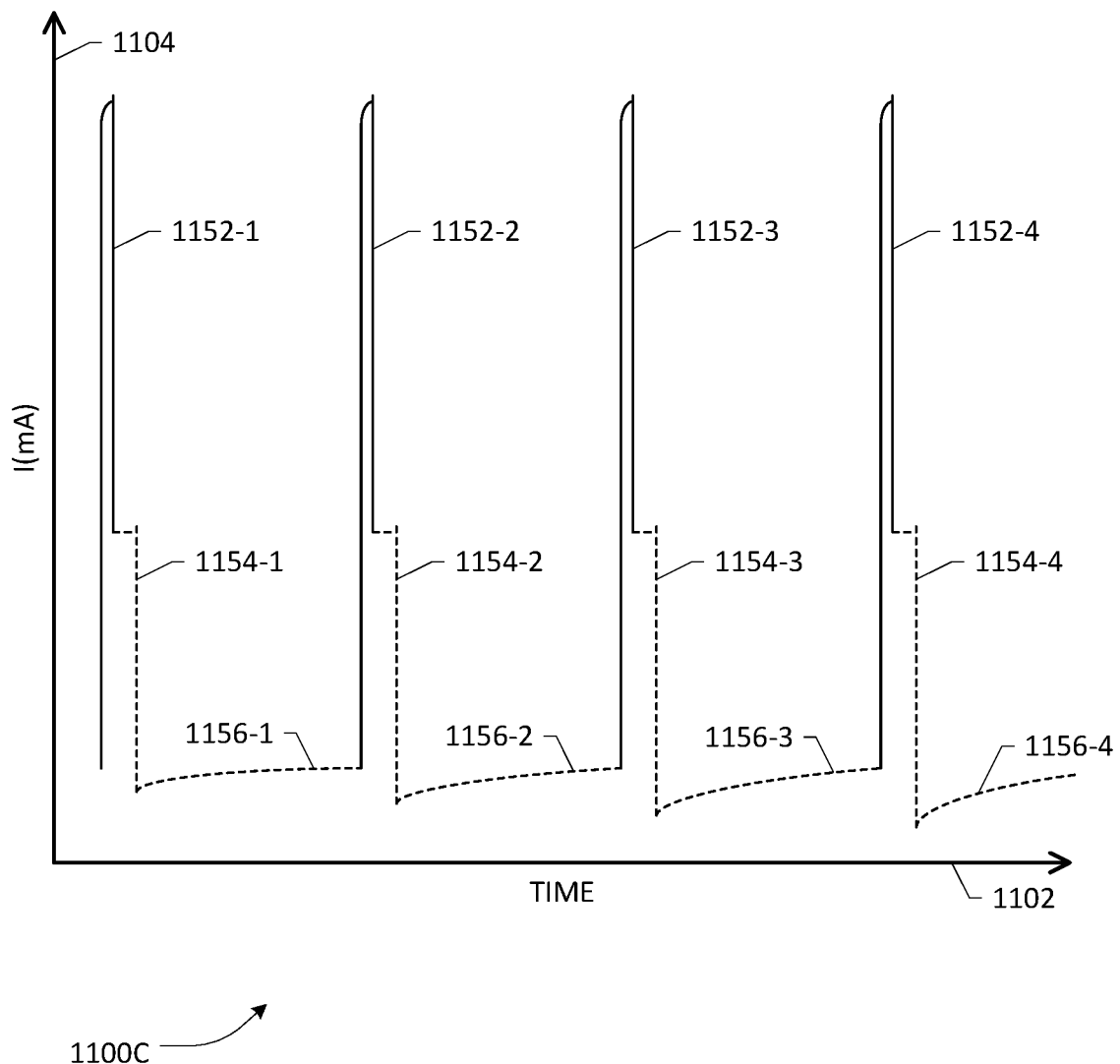

Turning to FIGS. 11A-11C, depicted therein are example waveform simulations associated with stimulation therapies according to some embodiments of the present disclosure. Panel 1100A shown in FIG. 11A is illustrative of stimulation current flow to two different electrode regions where passive discharge is allowed to occur simultaneously for both regions. In panel 1100A, an electrical parameter (e.g., current amplitude) and time are plotted on Y-axis 1104 and X-axis 1102, respectively, wherein stimulation pulses 1106-1 to 1106-3 represent a stimulation current flow to a first electrode region and stimulation pulses 1110-1 to 1110-3 represent a stimulation current flow to a second electrode region, each current flow being effectuated by a respective stimulation engine. Although both stimulation current waveforms are exemplified in panel 1100A with the same amplitude, pulse width, and frequency (but with a phase difference), example embodiments may be configured to provide current flows having waveforms with different frequencies, pulse widths, and/or amplitudes. Passive discharge of the first electrode region energized by the pulses 1106-1 to 1106-3 is shown as RC delay portions 1108-1 to 1108-3 of the waveform, whereas passive discharge of the second electrode region energized by the pulses 1110-1 to 1110-3 is shown as RC delay portions 1112-1 to 1112-3 of the corresponding waveform. It should be appreciated that the RC delay portions of the waveforms corresponding to both electrode regions can occur at the same time (e.g., overlapping discharge). Allowing more than one set of electrodes to discharge at a time can expand the capability of passive discharge programs commonly used in certain stimulation therapies, such as, e.g., DBS therapy, multi-stim burst pulse therapy for chronic pain, etc.

Panel 1100B shown in FIG. 11B is illustrative of a scenario where independent or different electrical parameters are programmed for stimulating two different electrode regions by corresponding stimulation engines respectively. Stimulation pulses 1122-1 to 1122-3 having a first frequency ($F_1$) and first current amplitude ($AMP_1$) and subsequent RC discharge portions 1123-1 to 1123-3 represent one stimulation waveform with respect to a first set of electrodes. Stimulation pulses 1124-1 to 1124-6 having a second frequency ($F_2$) and second current amplitude ($AMP_2$) and subsequent RC discharge portions 1125-1 to 1125-6 represent a second stimulation waveform with respect to a second set of electrodes, wherein $F_2 > F_1$ and $AMP_1 > AMP_2$. Similar to the discharge programs shown in FIG. 11A, the respective discharge portions of the two programmed current waveforms shown in panel 1100B of FIG. 11B may overlap. Further, there may be a situation where one or more of the respective pulse trains may also overlap depending on the programmed frequencies, e.g., as illustrated by the overlapping pulse 1122-2 of the first waveform and pulse 1124-3 of the second waveform. However, programmed currents and passive discharge for the two electrode regions are handled correctly without any scheduling for avoiding collisions in an example embodiment of the present patent disclosure. Since a single common VM is provided for supplying voltage to multiple stimulation engines, a common VM target output voltage setting must be used when pulse collisions, i.e., overlapping pulses, do occur. This may cause a reduction in stimulation efficiency when two pulses having different amplitudes are to be delivered at the same time wherein one VM voltage setting may be suboptimal. However, an acceptable trade-off of the VM settings may be achieved because such collisions are generally a rare occurrence or can be designed to be so (e.g., by varying the programmed frequencies of the two waveforms) in a therapy application.

Panel 11000 shown in FIG. 11C is illustrative of a scenario where multiple stimulation engines are assigned to the same electrode set or region and each respective stimulation engine is programmed to supply a corresponding stimulation waveform. Due to the principle in electrophysics that all stimulation currents which flow in/out of a node simply add or subtract because of conservation of charge, a more complex waveform may be provided to the electrode set that is constructed from the simultaneous application of the individual waveforms by the respective stimulation engines. For example, in one embodiment, a variety of complex waveforms may be built using simple frequency domain programming for respective engines in a therapy application (i.e., "waveform stacking", "waveform nesting" or "waveform engineering"). In FIG. 11C, panel 1100C exemplifies a resultant waveform constructed from two separate waveforms each having different amplitudes but the same frequency, wherein "stair-step" pulses each comprising an amplitude from the pulse of the first waveform as well as an amplitude from the pulse of the second waveform are shown. By way of example, pulse portions 1152-1 to 1152-4 (having a larger amplitude) and pulse portions 1154-1 to 1154-4 (having a smaller amplitude) are combined to generate respective stair-step pulses provided to the select electrode region, which may be programmed to discharge passively having a combined RC delay portion that follows the stair-step pulse, e.g., as represented by composite decay portions 1156-1 to 1156-4.

FIGS. 12A and 12B each depict a panel of waveforms associated respectively with a single engine stimulation therapy based on pulse shifting and a two-engine stimulation therapy according to an embodiment of the present patent disclosure. Panel 1200A shown in FIG. 12A exemplifies a scenario where a single stimulation engine is used for providing different stimulation waveforms 1202, 1204 to two different electrode sets, Region A and Region B. Because the stimulation engine having the single current sink cannot output more than one current at a time, the stimulation engine is programmed to shift pulses 1208 of the waveform 1204 (thereby causing time-shifting of pulses, also referred to as pulse scheduling) in order to avoid pulse collision between the respective pulses of the corresponding waveforms. As shown in FIG. 12A, time intervals 1206-1 to 1206-3 represent the shifted portions of the waveform 1204 that allow or accommodate the pulsing signals 1203-1 to 1203-3 of the waveform 1202 supplied to Region A. Such pulse shifting can cause distortion of the delivered frequency, thereby potentially compromising the intended therapeutic benefit. Additionally, such shifting also complicates the design of external programming/instrumentation in addition to causing increased power drainage in the IMD/IPG.

Panel 1200B shown in FIG. 12B exemplifies a scenario where two stimulation engines are advantageously programmed for providing different stimulation waveforms 1202, 1212 to two different electrode sets, Region A and Region B, without having to resort to pulse scheduling. As shown, pulses 1208 of the waveform 1212 provided to Region B may occur while the pulsing signals 1203-1 to 1203-3 of the waveform 1202 are also being delivered to Region A, as illustrated by overlapping timing intervals 1214-1 to 1214-3.

Based on the foregoing, it should be appreciated that embodiments herein provide a circuit implementation scheme that advantageously allows for multiple SEs to stimulation currents to be output at any time by any SE, even simultaneously, without the risk of encountering therapy delivery issues due to stimulation therapy collisions. Example embodiments may be configured to improve compatibility and ease of programming/control of therapy delivery with emerging complex stimulation programs where it would otherwise become increasingly difficult to predict and to avoid therapy collisions, which typically occur in multi-frequency, multi-lead applications such as, e.g., dual brain hemisphere DBS therapies. Accordingly, example embodiments of the present invention may be practiced in a variety of therapy applications including but not limited SCS therapy, DBS therapy, DRG therapy, cochlear stimulation therapy, drug delivery therapy, cardiac pacemaker therapy, cardioverter-defibrillator therapy, cardiac rhythm management (CRM) therapy, an electrophysiology (EP) mapping and radio frequency (RF) ablation therapy, electroconvulsive therapy (ECT), repetitive transcranial (rTMS) magnetic stimulation therapy, and vagal nerve stimulation (VNS) therapy, and the like.

Additional advantages of the present invention may be particularly appreciated in view of the following. In the existing neurostimulator IPG implementations, all stimulation engine circuitry is powered with its negative power supply reference being the negative battery terminal of the IPG. This can prevent multiple stimulation engines from each outputting optimal stimulation therapies, since only a single voltage multiplier output voltage can be output to human tissue at any one time via the anode electrode. In other words, multiple anode electrode voltages that are different (which may be needed to optimize battery current efficiency for each stimulation engine) cannot "collide" as they are simultaneously output to human tissue. Should such a collision or contention occur over a lead system, unintended stimulation currents can flow between the anode electrodes at different voltages. Existing neurostimulator IPGs are unable to avoid those kinds of stimulation "collisions", resulting in at least one non-optimal shared voltage multiplier setting necessary for the simultaneous delivery of therapy with multiple stimulation engines. In contrast, example embodiments herein provide a multi-SE arrangement wherein each SE is independently powered, typically from a charge pump capacitor charged to the battery voltage, which allows each SE to independently operate at optimum stimulation efficiency. Further, in some embodiments, electrodes or electrode sets may configured for stimulation by independent SEs to provide therapy to different areas of the patient's tissue. In still further embodiments, two or more electrodes or electrode sets may be commonly stimulated by two or more SEs to provide nested stimulation therapy to at least a portion of the patient's tissue.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, some example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Various types of switching circuit blocks as well as associated control logic signals as set forth in the example embodiments may be implemented in myriad ways using a broad range of electronic devices known in the electrical arts, e.g., including but not limited to bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, diodes, and the like, as well as any digital logic gates built therefrom. It will be further understood that the sizing (e.g., channel width and length) and biasing of the switching devices is highly configurable, e.g., depending on whether anodic current stimulation or cathodic stimulation current is being programmed (i.e., whether the electrodes of a lead system are configured to operate as current sink terminals or cathodes, or as current source terminals or anodes) as well as how much current is to be carried for each electrode set (i.e., granularity and distribution of the currents drawn from respective loads).

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A stimulation therapy method using an implantable medical device (IMD), the IMD including a power supply and a lead system of one or more leads configured to be positioned proximate to a tissue of a patient, wherein the one or more leads includes a plurality of electrodes, the method comprising:
providing a voltage multiplier (VM) configured to generate a range of target voltages at an output node based on a voltage supplied by the power supply;
providing a plurality of stimulation engines (SE) individually configured to support an anodic node and a cathodic node, wherein, for at least one SE:
the anodic node is switchably connectable by first switching circuitry to a VM connection node driven by the output node, the first switching circuitry configured to:
in an active state of the at least one SE, connect the anodic node to the VM connection node to receive the voltage supplied by the power supply; and
in an inactive state of the at least one SE, disconnect the anodic node from the VM connection node;
the cathodic node is switchably connectable by second switching circuitry to a current sink circuit operative to drive the cathodic node; and
a discharge switching circuitry is disposed between the anodic node and the cathodic node;
selectively coupling one or more sets of electrodes of the lead system to a corresponding number of SEs at respective anodic and cathodic nodes;
providing, for the at least one SE, a current source circuit, wherein the first switching circuitry is arranged to switch the anodic node of the SE between a direct connection to the VM connection node and another connection to the VM connection node via the current source circuit; and
generating a plurality of control signals for independently controlling at least some of the SEs such that the at least some of the SEs are activated to stimulate or discharge a corresponding set of electrodes independently from or in concert with remaining SEs for applying a stimulation therapy to the tissue according to a stimulation set, wherein channel contention between sets of electrodes of the lead system is avoided.

2. The method as recited in claim 1, further comprising generating, for a respective SE, a first control signal for controlling the first switching circuitry, a second control signal for controlling the second switching circuitry and a third control signal for controlling the discharge switching circuitry of the respective SE.

3. The method as recited in claim 2, wherein the first and second control signals are asserted for a select SE, in a stimulation mode, to enable the first switching circuitry and the second switching circuitry of the select SE for reconnecting the VM connection node to the anodic node and the current sink circuit to the cathodic node to facilitate stimulation of a corresponding select set of the electrodes and the third control signal is de-asserted to disable the discharge switching circuitry of the select SE.

4. The method as recited in claim 2, wherein the first and second control signals are de-asserted for a select SE, in a discharge mode, to disable the first switching circuitry and the second switching circuitry of the select SE for disconnecting the VM connection node from the anodic node and the current sink circuit from the cathodic node, and the third control signal is asserted to enable the discharge switching circuitry of the select SE for facilitating passive discharge of a corresponding select set of the electrodes.

5. The method as recited in claim 1, further comprising generating, for a respective SE, a first pair of control signals for controlling the first switching circuitry, a second pair of control signals for controlling the second switching circuitry, the second pair of control signals having complementary logic levels with respect to the first pair of control signals, and a third control signal for controlling the discharge switching circuitry of the respective SE.

6. The method as recited in claim 5, wherein the first pair of control signals and the second pair of control signals are asserted with first logic levels, for a select SE in a stimulation mode, to enable the first and second switching circuitry of the select SE for connecting the VM connection node to the anodic node and the current sink circuit to the cathodic node to facilitate stimulation of a corresponding select set of the electrodes and the third control signal is de-asserted to disable the discharge switching circuitry of the select SE.

7. The method as recited in claim 5, wherein the first pair of control signals and the second pair of control signals are de-asserted with second logic levels, for a select SE in a discharge mode, to disable connections of the select SE to the anodic node and the cathodic node, and the third control signal is asserted to enable the discharge switching circuitry of the select SE for facilitating passive discharge of a corresponding select set of the electrodes.

8. The method as recited in claim 1, wherein the stimulation therapy comprises a select set of properties including at least one of a stimulation frequency, a stimulation pulse width, a stimulation pulse amplitude, a discharge method, or phase information.

9. The method as recited in claim 1, wherein the stimulation therapy comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial (rTMS) magnetic stimulation therapy, or a vagal nerve stimulation (VNS) therapy.

10. The method as recited in claim 1, wherein the sets of electrodes are configured for stimulation by independent SEs to provide therapy to different areas of the tissue.

11. The method as recited in claim 1, wherein an electrode set is commonly stimulated by two or more SEs to provide nested stimulation therapy to at least a portion of the tissue.

12. A stimulation therapy method using an implantable medical device (IMD), the IMD including a power supply and a lead system of a plurality of electrodes configured to be positioned proximate to a tissue of a patient, the method comprising:
  generating a range of target voltages at an output node of a voltage multiplier (VM);
  providing a plurality of stimulation engines (SE) individually configured to support an anodic node and a cathodic node, wherein, for an SE of the plurality of SEs:
    the anodic node is switchably connectable, via a first switching circuitry, to a VM connection node driven by the output node;
    the cathodic node is switchably connectable to a current sink circuit operative to drive the cathodic node; and
    a discharge switching circuitry is disposed between the anodic node and the cathodic node;
  selectively coupling one or more sets of electrodes of the lead system to a corresponding number of SEs at respective anodic nodes and cathodic nodes;
  providing, for at least one SE of the plurality of SEs, a current source circuit, wherein the first switching circuitry is arranged to switch the anodic node of the at least one SE between a direct connection to the VM connection node and another connection to the VM connection node via the current source circuit; and
  generating a plurality of control signals for independently controlling at least some of the SEs such that the at least some of the SEs are activated to stimulate or discharge a corresponding set of electrodes independently from or in concert with remaining SEs for applying a stimulation therapy to different areas of the tissue.

\* \* \* \* \*